(12) United States Patent
Hobet et al.

(10) Patent No.: US 7,950,971 B2
(45) Date of Patent: May 31, 2011

(54) ELECTRICAL CONNECTOR APPARATUS AND METHODS

(75) Inventors: Anatolie Hobet, Salem, OR (US);
Donald J. Brooks, San Diego, CA (US)

(73) Assignee: CardioDynamics International Corporation, Bothell, WA (US)

( * ) Notice: Subject to any disclaimer, the term of this patent is extended or adjusted under 35 U.S.C. 154(b) by 94 days.

(21) Appl. No.: 12/221,949

(22) Filed: Aug. 8, 2008

(65) Prior Publication Data

US 2010/0036231 A1 Feb. 11, 2010

(51) Int. Cl.
*H01R 4/48* (2006.01)
(52) U.S. Cl. ......................................... 439/822; 439/909
(58) Field of Classification Search .................. 439/729, 439/822, 759, 506, 909, 828, 829, 789; 600/394
See application file for complete search history.

(56) References Cited

U.S. PATENT DOCUMENTS

| | | | |
|---|---|---|---|
| 1,212,821 A | 1/1917 | Schade | |
| 1,393,139 A * | 10/1921 | Kiesel, Jr. ................ | 384/190.6 |
| 2,036,461 A * | 4/1936 | Darby ........................... | 132/220 |
| 2,522,810 A * | 9/1950 | Bailey ........................... | 439/729 |
| 2,758,947 A | 8/1956 | Feighner | |
| 3,740,703 A * | 6/1973 | Sessions ....................... | 439/822 |
| 3,774,143 A | 11/1973 | Lopin | |
| 4,040,697 A | 8/1977 | Ramsay et al. | |
| 4,178,052 A | 12/1979 | Ekbom et al. | |
| 4,206,960 A | 6/1980 | Tantillo et al. | |
| 4,220,387 A | 9/1980 | Biche et al. | |
| 4,303,293 A * | 12/1981 | Grunwald .................... | 439/263 |
| 4,637,672 A * | 1/1987 | Peterman et al. ............ | 439/592 |
| 4,671,591 A | 6/1987 | Archer | |
| 5,277,613 A | 1/1994 | Neward | |
| 5,442,975 A * | 8/1995 | Osborn ....................... | 74/473.21 |
| 5,571,145 A * | 11/1996 | Drebin ............................ | 607/37 |
| 5,791,944 A * | 8/1998 | Grant et al. ................... | 439/822 |
| 5,895,298 A | 4/1999 | Faupel et al. | |
| 6,142,949 A | 11/2000 | Ubby | |
| 6,487,430 B1 * | 11/2002 | Henderson et al. ........... | 600/394 |
| 6,561,986 B2 | 5/2003 | Baura et al. | |
| 6,602,201 B1 | 8/2003 | Hepp et al. | |

(Continued)

FOREIGN PATENT DOCUMENTS

FR  964611  8/1950

*Primary Examiner* — Neil Abrams
(74) *Attorney, Agent, or Firm* — Perkins Coie LLP

(57) ABSTRACT

Size-specific electrical connector apparatus optimized for e.g., biomedical applications, and which prevents mating to the wrong sized terminals. In one embodiment, the connector apparatus comprises a device having a two piece assembly adapted to pivotally engage and lock a sensor such as those used in impedance cardiography (ICG). The conductor is shaped so as to provide a high degree of specificity in sensor connection as well as signal stability and reliability. In one variant, the pivot comprises a spring-loaded pivot having no external stops and the shape of a sensor engaging aperture is defined by a metal insert associated with one element of the assembly and the pivot is permanently formed within the connector. Thus, a user is obstructed from changing the properties of the connector to accept smaller or larger sensors. Methods of manufacturing and operating the connector are also disclosed. In one embodiment, an opening in the metal insert (212) is sized to exclude oversized sensors. In another embodiment, a V-shaped stop (308) on one of the elements (304) acts to limit closure and to prevent a tight grip upon an undersized sensor.

40 Claims, 22 Drawing Sheets

U.S. PATENT DOCUMENTS

| | | |
|---|---|---|
| 6,636,754 B1 | 10/2003 | Baura et al. |
| 7,043,293 B1 | 5/2006 | Baura |
| 7,083,480 B2 * | 8/2006 | Silber ................ 439/835 |
| 7,149,576 B1 | 12/2006 | Baura et al. |
| 7,214,107 B2 | 5/2007 | Powell et al. |
| 7,251,524 B1 | 7/2007 | Hepp et al. |
| 7,270,580 B2 | 9/2007 | Bradley |
| 7,570,989 B2 | 8/2009 | Baura |
| 7,740,510 B2 * | 6/2010 | Muz ........................ 439/759 |
| 2003/0068914 A1 | 4/2003 | Merry et al. |
| 2004/0039275 A1 | 2/2004 | Sato et al. |
| 2004/0072475 A1 | 4/2004 | Istvan |
| 2004/0106964 A1 | 6/2004 | Fischer et al. |
| 2004/0243192 A1 | 12/2004 | Hepp |

* cited by examiner

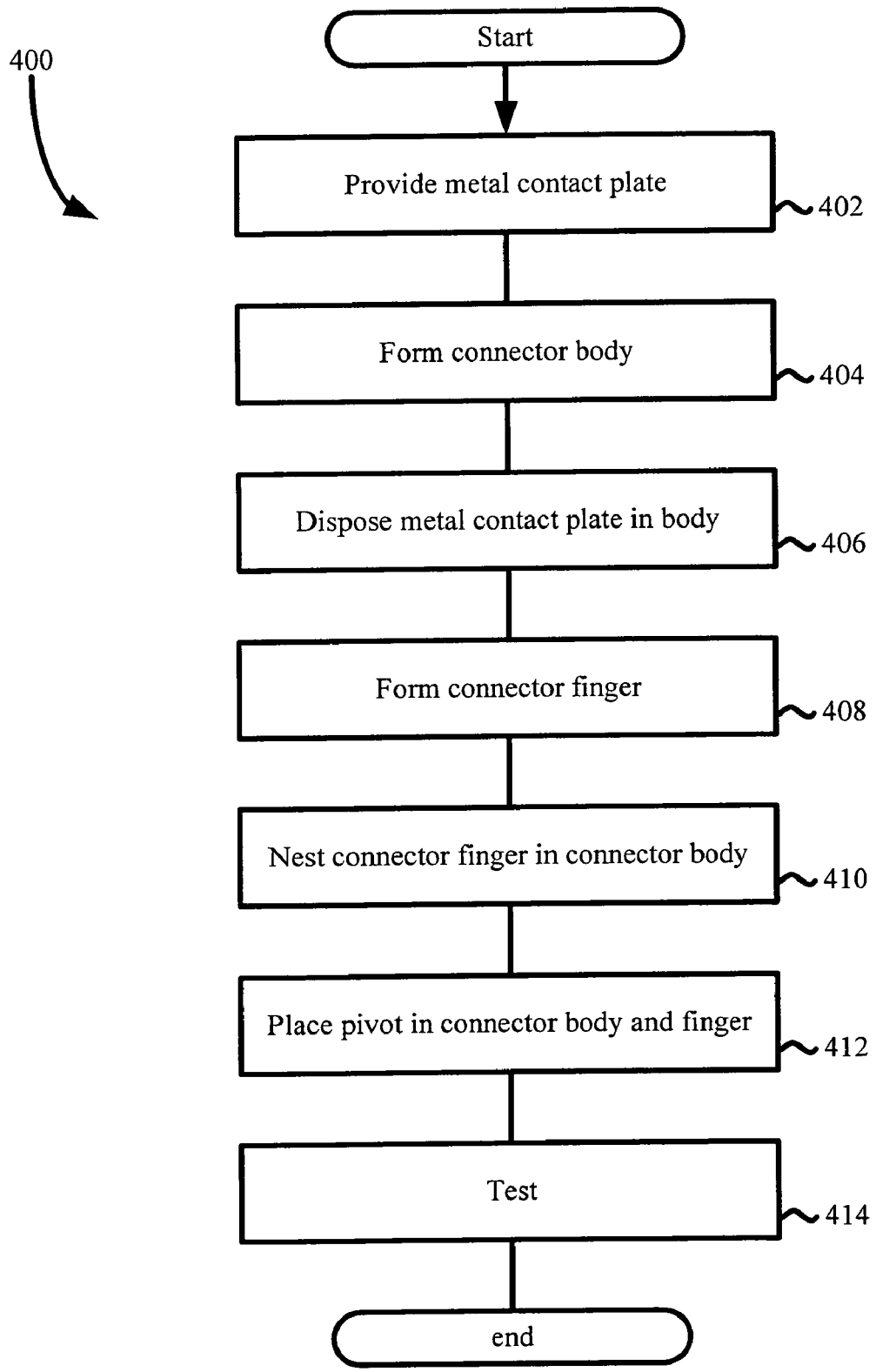

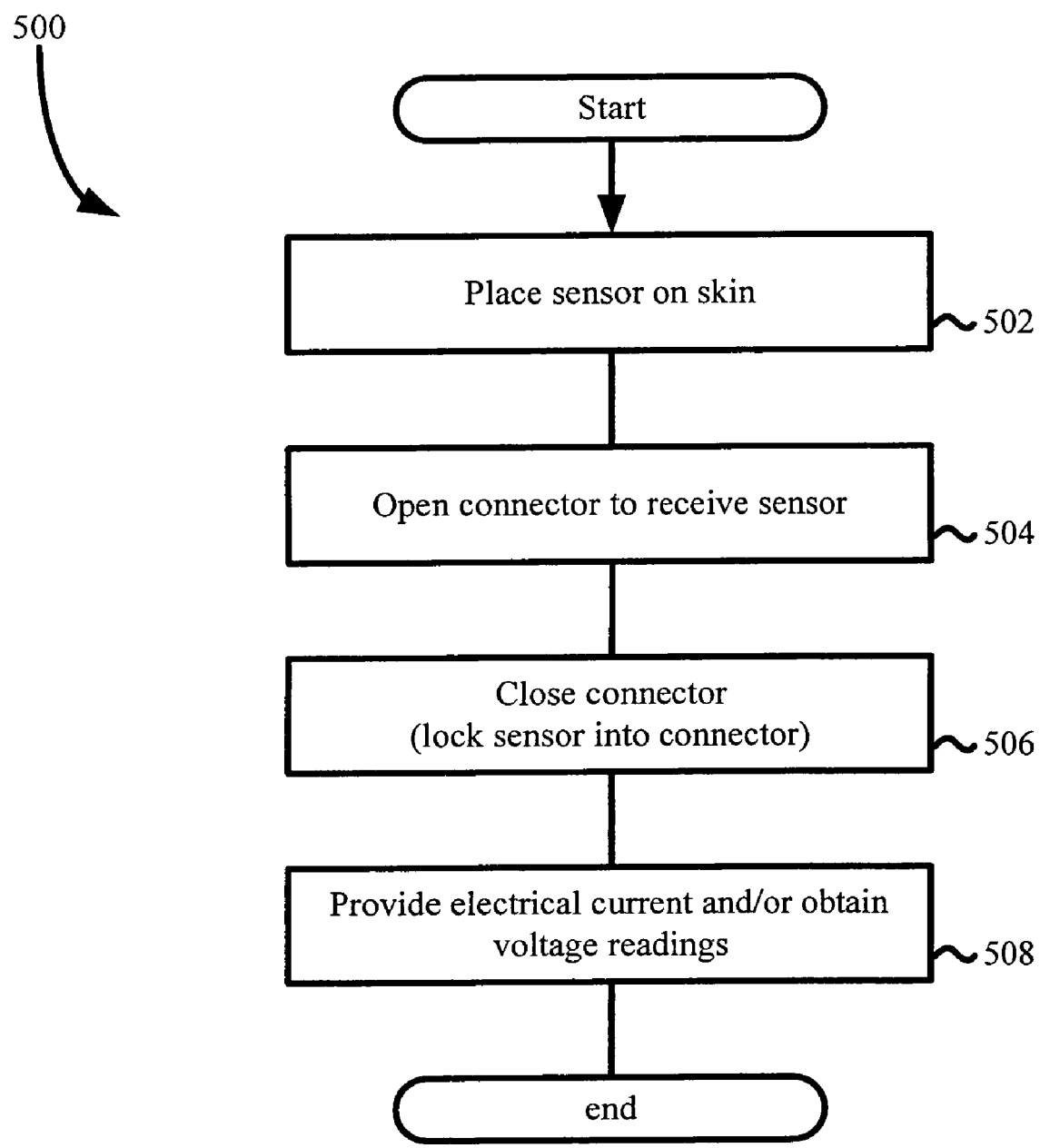

ELECTRICAL CONNECTOR APPARATUS AND METHODS

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

1. Field of the Invention

The present invention relates generally to the field of electrical connectors and connection apparatus, and particularly in one aspect to an electrical connector apparatus useful in, inter alia, biomedical applications.

2. Description of Related Technology

In certain electrical connector applications, multiple (often competing) design and performance requirements exist, thereby significantly constraining the selection of connector technology for use in that application. This is especially true of certain clinical or biomedical applications such as impedance cardiography (ICG) and electrocardiography (ECG), wherein it is highly desirable to have a connector which is low cost, clinically rugged and robust, yet which provides both acceptable electrical performance (including low impedance) in a stable and repeatable manner. ICG and ECG connector assemblies have been historically characterized by high cost and substantial complexity of design. Unfortunately, such high cost tends to steer the clinician (or medical facility) using the connector to use the connector in an unintended manner. For example, a clinician may attempt to use a single connector for both ECG and ICG measurements. Such uses however do not produce ideal results and create significant barriers to adoption of the technology in the first place.

Ensuring a clinician employs a correct ICG or ECG connector assembly for a particular sensor is also crucial when the clinician utilizes methods which include the simultaneous operation of ECG and ICG. One exemplary method requiring simultaneous operation of ECG and ICG is described in co-owned U.S. Pat. No. 7,270,580 issued Sep. 18, 2007 and entitled "Methods and Apparatus for Conducting Electrical Current", which is incorporated by reference in its entirety. As disclosed therein, an electrode having at least two sensors of differing size disposed thereon is used; at least one of the sensors is adapted to be operated with an ICG connector assembly and the other for an ECG connector assembly. The electrode enables clinicians to apply ICG methods to measure a stroke volume, which is then multiplied by heart rate measurements obtained by ECG methods to obtain a cardiac output measurement.

Generally, in ICG applications sensors are disposed on the neck and chest of a patient to transmit and detect electrical and impedance changes in the thorax. The impedance measurements are then used to measure and calculate hemodynamic parameters. As indicated, one sensor is used for transmitting electrical current through the chest, while the other is used to detect or sense voltage. The sensors comprise at least two different sizes to facilitate coupling of connectors to the sensors in the correct orientation. In other words, the different sized sensors prevent connectors (and electric components associated therewith) from being inadvertently coupled to the wrong sensor. Accordingly, exemplary ICG connectors would be very simple in construction and low in cost, yet unique to the particular ICG sensor that it belongs (e.g., either the current source or the voltage sensor). Thereby providing accurate measurements and prevent misuse, including misuse of ICG connectors for ECG sensors.

Another consideration especially for biomedical applications relates to so-called "pull away" force. In accordance with standards set forth in by the American National Standards Institute (ANSI) and Association for the Advancement of Medical Instruments (AAMI) for ECG cables and electrical wires (ANSI/AAMI EC 53-1995 ECG Cables and Lead Wires Standard), which is incorporated herein by reference in its entirety, an ECG connector must be adapted to break free or pull away at a certain force (e.g., when the ECG equipment and the patient having sensors and a connector mounted on are pulled away from one another). The standard defines that when such an event occurs, the connector and its cables break away from the sensors disposed on the patient and do not remain hanging from the sensors on the patient, but rather are adapted to detach as a unit from the sensors. This requirement is intended to maintain the electrical safety of the patients and clinicians; e.g., so that the free ends of the leads can not be inadvertently or intentionally plugged into another piece or equipment or otherwise present an electrical shock or grounding hazard. Hence, a connector for use in such applications must be designed so as to provide the requisite electrical contact and low-impedance interface, be rugged and positive in its mating, yet pull off the sensor (terminal) at a force below that which would cause the cables to be dissociated from the parent ECG equipment.

A great variety of different electrical connector designs (biomedical and otherwise) are known in the prior art, the following being generally representative.

U.S. Pat. No. 1,212,821 to Schade discloses a device for spring fastening a wire device to an electrical conductor.

U.S. Pat. No. 2,758,947 to Feighner discloses a method of clamping a spring loaded clip onto wires, terminals or other electrical conductors.

French Patent No. 964,611 to Ford issued August 1950 discloses a metallic loop element with aperture adapted for mating with a spark plug electrode. The loop is expanded by biasing two portions of the loop toward one another.

U.S. Pat. No. 3,774,143 to Lopin discloses an adapter for use in making an electrical connection between an electrode and a cable connected to a monitoring instrument.

U.S. Pat. No. 4,040,697 to Ramsay, et al. issued Aug. 9, 1977 entitled "Electrical connector" discloses an electrical connector that has a resilient, stamped, metallic leaf contact defining a narrow neck contact entrance area and having reversely bent ends on either side of said area. A plastic body section embeds the ends and spans the area to provide two side by side lever legs arranged to act so that pressure on the legs resiliently opens the narrow neck to allow entrance of a second body contact. Relaxation of pressure on the legs causes resilient action of the connector to provide gripping of the second contact with a positive three point grip.

U.S. Pat. No. 4,178,052 to Ekbom, et al. issued Dec. 11, 1979 entitled "Medical terminal clip member for attachment to patient electrodes" discloses a medical terminal clip that has a body member with a longitudinal axis and a pair of laterally spaced leg members extending in approximately the longitudinal direction and pivotally connected for relative movement. The respective spaced leg members form a variably spaced electrode receptacle on one side of the pivotal connection. A beryllium copper conductive member is embedded in the body member and is formed from a strip of metal bent into approximately an M-shape with side flanges on the leg members to ostensibly provide additional strength. A shield or barrier member extends at least between the approximate ends of the leg members on the other side of the pivotal connection while permitting relative movement of the leg members. The shield member is designed to close longitudinal access to the space between the leg members and thereby prevent any dislocation of the terminal clip member by catching onto exterior objects such as other terminal wires.

U.S. Pat. No. 4,206,960 to Tantillo, et al. issued Jun. 10, 1980 entitled "Electrical connector" discloses an electrical connector for engaging a terminal stud that has first and second insulating spring arms each carrying a conductive metal contact with the metal contacts defining through holes for electrically contacting a shank of a terminal stud. The metal contacts normally are in opposed spaced relationship to each other but are superimposed over each other and resiliently biased to their original position when the spring arms are squeezed toward each other by finger pressure. Release of the pressure causes the contacts to grasp the shank of a terminal stud over which the contacts are positioned. An electrical connector is formed by positioning a preformed end piece over an insulated wire and then molding a plastic connector end in abutting relationship with at least a portion of said preform whereby the molding and forming temperature used does not adversely affect the insulation of said wire.

U.S. Pat. No. 4,220,387 to Biche, et al. issued Sep. 2, 1980 entitled "Medical clip" discloses a medical terminal, particularly for use in connecting a lead wire or conductor to an electrode conventionally secured to the skin surface of a human or animal. The electrode comprises a male projection of the buttontype with an enlarged diameter head portion disposed within a recessed area of the electrode. The clip is generally V or wishbone shaped and includes a pair of support arms secured together at one end and normally spaced from each other at the other end. The arms carry resilient conductive loops normally biased out of overlapping condition but movable upon the application of external force into an overlapped condition wherein the clip may be applied over the head portion of the electrode. The support arms have offset depending shoulder portions from which the conductive loops extend and which are positionable within the recessed area of the electrode when the arms are moved toward each other. The support arms are integrally formed of resilient dielectric plastic material in an initial unstressed generally V-shape, with a female socket embedded in the plastic and electrically connected by conductor means to the conductive loops. Replaceable or interchangeable identification means is removably mounted on the clip in the area of the female socket, and a strain relief cover is removably positionable on the clip over said female socket and over said identification means to provide strain relief for the connection to a lead wire, and the cover is at least in part transparent to provide visual observation of the identification means.

U.S. Pat. No. 4,671,591 to Archer issued Jun. 9, 1987 entitled "Electrical connector" discloses a connector for establishing electrical connection between a conductor and a patient engaging electrode that includes a conductive post extending from the electrode. The post has a proximal portion, a distal portion, and an intermediate portion having a diameter smaller than the diameter of the distal portion. The connector comprises insulation means shaped to form a socket open at one end, a pair of first spring members, a pair of second spring members, and means for electrically connecting the conductor to the second spring members. The first spring members are laterally positioned with respect to one another in the socket, and the second spring members are laterally positioned with respect to one another in the socket closer to said one end than the first spring members. The first and second spring members are positioned and constructed such that when the post is inserted in the socket, the second spring members grip the proximal portion of the post, and the first spring members and the intermediate and distal portions of the post comprise a detent mechanism that resists removal of the post from the socket.

U.S. Pat. No. 5,277,613 to Neward issued Jan. 11, 1994 entitled "Electrode junction assembly" discloses an electrical junction block particularly for use with a fetal electrode and electronic monitor. The junction block comprises a housing having a cavity therein, and a substantially U-shaped spring disposed in the cavity. The spring has legs which are biased outwardly by a suitable coil spring. The housing contains electrical contacts and wires connected thereto, and the U-shaped spring can be depressed to provide openings for receiving electrode wires. A mounting pad can be disposed on the housing for facilitating mounting of the assembly on a person during use.

U.S. Pat. No. 5,895,298 to Faupel, et al. issued Apr. 20, 1999 entitled "DC biopotential electrode connector and connector condition sensor" discloses an electrode connector and connector condition sensor for a biopotential sensing apparatus. A plurality of electrodes are connected to individual output leads for individual electrode channels by a connector which does not abrade the surface of the electrode button contact and does not require that pressure be applied to the electrode during connection. Two spring biased conductive arms for the connector are spread apart by the cam surface of an actuator button to receive the button contact and are contoured to engage substantially the peripheral surface of the button contact when the actuator button is released. The biopotential sensing apparatus includes a processor which senses the loss of signal in any electrode channel during a test period and activates an indicator to provide a warning indication.

U.S. Pat. No. 6,142,949 to Ubby issued Nov. 7, 2000 entitled "Lead protection and identification system" discloses a lead protection and identification system for a medical diagnostic device. Electrodes are placed on predetermined locations of a patient, and the system includes clips for attaching to the electrodes. The system identifies a lead and provides information to a user as to which one of the electrodes the lead should be connected to. Potentially dangerous signals are prevented from being inputted to a clip when the clip is not connected to an electrode and prevents the patient from being injured.

United States Patent Publication No. 20030068914 to Merry, et al. published Apr. 10, 2003 entitled "Precordial electrocardiogram electrode connector" discloses an electrocardiogram electrode connector for connecting an electrode to an electrocardiogram device. The connector of the present invention comprises a lower portion having an electrode end and an ECG end, and an upper portion pivotally connected to the lower portion. The upper portion likewise has an electrode end and an ECG end. The connector also comprises a spring between the lower portion and the upper portion to bias the electrode ends together to clamp about an electrode. Further, the connector comprises an electrical assembly having an elastomeric electrical connector to provide electrical continuity between the electrode and the ECG device when the electrode ends of the lower portion and the upper portion of the connector are biased together.

United States Patent Publication No. 20040039275 to Sato, et al. published Feb. 26, 2004 entitled "Biological electrode and connector for the same" discloses a conductive member adapted to be attached onto a living tissue to detect a bioelectrical signal. A retainer retains the conductive member on the living tissue. A lead member is partly brought into contact with the conductive member to lead out the bioelectrical signal to a connector. A waterproof sheet covers the lead member in a watertight manner, while exposing a portion of the lead member from which the biological signal is led out.

United States Patent Publication No. 20040072475 to Istvan published Apr. 15, 2004 entitled "Electrode connector" discloses an electrode connector for connecting a conventional tab electrode or sensor to a lead assembly for use with a physiological data collection system. The electrode connector includes a lead connecting portion for attaching the electrode connector to a lead assembly and a tab connection portion for attaching the electrode connector to a tab electrode or sensor. During use, the electrical signals corresponding to physiological data of the patient pass from the tab electrode or sensor, through the electrode connector, and to the lead assembly.

United States Patent Publication No. 20040106964 to Fischer, et al. published Jun. 3, 2004 entitled "Implantable Medical Device with Multiple Electrode Lead and Connector with Central Fastener" discloses an implantable medical device such as a cardiac stimulator, a multi-electrode lead attached to the device, and a connector coupling the device to the lead. The lead has multiple electrodes, each electrode connected to a wire extending though the lead. The electrodes may be circumferential coils or rings, for example. The lead has a connector that fits into a recess on a surface of the device or apparatus. A bottom wall of the recess has an array of apparatus connections deployed around a threaded bore. The connector is attached to the apparatus by a screw with a threaded shaft and an enlarged head. The screw passes through a central bore in the connector. Electrical connections form a regular pattern, such as a rectangular or square grid, or a radial pattern, around the central bore. A pair of O-rings or seals surround the connections. A gasket, mounted on male connections or contacts, fits around female connections that may be on either the apparatus or the connector.

Despite this broad variety of designs, what is needed is a connector which is inter alia uniquely adapted to the sensor or terminal it is to be used with so that the chances of using the connector and/or the terminal improperly are mitigated. An exemplary connector would also ideally be easy to use and provide optimal surface area contact between the sensor and connector. Likewise, the connector would substantially frustrate modification of the connector in order to provide connection to unintended sensors.

Further, an ideal connector would be adaptable to exhibit desired "pull-away" properties.

SUMMARY OF THE INVENTION

The present invention satisfies the aforementioned needs by providing an improved electrical connector apparatus and associated methods of use and manufacturing.

In a first aspect of the invention an electrical connector is disclosed. In one embodiment, the electrical connector is adapted for use with a biomedical sensor of a particular size, the connector comprising a first actuation element having at least one electrically conductive element associated therewith; a second actuation element, at least a portion of the second actuation element adapted to be mated with the first actuation element, the mating comprising forming at least one feature for receiving at least a portion of the sensor; and a pivot element adapted to enable the actuation elements to pivot with respect to one another, the pivoting causing an effective diameter of the feature for receiving at least a portion of the sensor to adjust; and wherein the pivot element is configured to ensure that, upon the pivoting of the actuation elements to their fully open position, the effective diameter of the feature is not greater than a pre-set amount.

In one variant, the pivot element is adapted to ensure that the diameter of the feature is not greater than the pre-set amount via one or more internal stopping features and the one or more internal stopping features are not accessible to a user of the connector when the actuation elements are mated.

In another variant, the pre-set amount comprises approximately 0.125 inches.

In still another variant, the pre-set amount comprises approximately 0.155 inches.

In still yet another variant, the mating of the actuation elements further comprises forming at least one channel adapted to receive the pivot element, and wherein the connection of the actuation elements by the pivot element comprises permanently receiving the pivot element within the channel and the pivot element in the channel is made permanent by an asymmetric shaped portion of the pivot element such that once the pivot element is received within the channel, the asymmetric portion substantially prevents the pin element from being removed.

In yet one more variant, the at least one electrically conductive element associated with the first actuation element comprises a metallic disk molded onto a surface thereof, the disk placed on the first actuation element so as to comprise at least a portion of the feature for receiving at least a portion of the sensor and the disk is at least partly chamfered along a contact surface thereof.

In another variant, the first actuation element further comprises at least one resistor disposed therein, the resistor adapted to dissipate energy and the at least one resistor does not dissipate more than ten percent (10%) of the total energy provided to the connector.

In still one more variant, the second actuation element further comprises at least one electrically conductive surface, the electrically conductive surface disposed proximate to the at least one feature for receiving at least a portion of the sensor.

In a second embodiment, the electrical connector is adapted to be employed in conjunction with a biomedical sensor and to have pull-away capabilities which are adjustable. The electrical connector comprises: at least two body elements adapted to be pivotally mated to one another, a first of the body elements having at least one electrically conductive portion, and the mating of the body elements causing formation of at least two apertures; and at least one spring-loaded pivot element adapted to be received within a first of the apertures and enabling the body elements to pivot with respect to one another, the pivoting of the body elements causing a second of the apertures to be widened and narrowed. The second aperture is adapted to removably receive at least a portion of the sensor therein, the widening of the second aperture enabling the at least a portion of the sensor to be received or removed and the narrowing of the second aperture enabling a sensor received therein to be substantially secured in place, and modification of one or more components of the connector apparatus causes adjustment of an amount of force required to dislodge the electrical connector from the sensor.

In one variant, the amount of force required to dislodge the electrical connector from the sensor is adjusted to cause the connector to conform with the pull-away requirements of the ANSI/AAMI EC 53-1995 Standard.

In another variant, the one or more components comprises at least the electrically conductive portion of the first body element, and wherein the modification comprises at least one of: chamfering at least a portion of the electrically conductive portion; or changing the shape of the electrically conductive portion.

In still another variant, a second of the body elements comprises, proximate to the second aperture, at least one mechanism for restraining the received sensor; and the sensor comprises at least a shaft portion and a cap portion, the shaft portion having a first diameter smaller than a diameter of the cap portion and wherein the at least one mechanism for restraining the at least a portion of the sensor comprises a substantially V-shaped extension of the second body element, the substantially V-shaped extension adapted to receive the sensor proximate to a junction between the cap and the shaft portion of the sensor, and the substantially V-shaped extension is further adapted to push the sensor into contact with the electrically conductive portion of the first body element.

In yet another variant, the at least one mechanism for restraining the sensor further comprises an electrically conductive portion.

In still yet another variant, the one or more components comprises at least the second body element, and the modification comprises changing the shape of the at least one mechanism for restraining.

In another variant, the one or more components comprises the spring-loaded pivot element, and wherein the modification comprises changing the tension of the spring-loaded pivot element.

In another variant, the receipt of the at least one spring-loaded pivot element into the first aperture is effected by the spring-loaded pivot element comprising a shape having one or more angular features adapted to interact with the aperture to substantially frustrate removal of the pivot element after insertion into the aperture.

In a third embodiment, the electrical connector is adapted for use with a biomedical sensor comprising at least one terminal composed of a shaft portion and a crown portion disposed at one end of the shaft portion, the crown portion having a greater diameter than the shaft portion, and the electrical connector comprises: two pivotally mated elements: the first element comprising at least one electrically conductive region adapted to accept at least a portion of the sensor terminal; and the second moveable element comprising at least one terminal confining region, the terminal confining region adapted to substantially maintain the position of the terminal relative the first moveable element via application of force against the shaft portion of the terminal; at least one pivot element about which the moveable elements are adapted to pivot; and at least one pivot obstruction feature adapted to impede the pivoting of the moveable elements in at least one direction, the pivot obstruction feature limiting the movement of the moveable elements such that they may pivot no more than a distance substantially equal to the diameter of the crown portion of the sensor.

In one variant, the diameter of the crown portion is approximately 0.125 inches.

In another variant, the diameter of the crown portion is approximately 0.155 inches.

In still another variant, the force applied to the sensor by the second moveable element comprises a force generated by a spring associated with the pivot element.

In yet another variant, the pivot element is permanently disposed within an opening formed by the mating of the moveable elements, the pivot element comprising at least one asymmetric region, the asymmetric region allowing the pivot element to be inserted within the opening, but also frustrating removal of the pivot element from the opening.

In another variant, the second moveable element further comprises an electrically conductive surface disposed proximate to the terminal confining region.

In still another variant, the first moveable element further comprises at least one resistor, the resistor adapted to dissipate defibrillation or other electrical energy in accordance with the requirements of the ANSI/AAMI EC 53-1995 Standard.

In still yet another variant, the at least one electrically conductive region of the first moveable element comprises a metallic plate molded onto a surface thereof, the plate having a cross-sectional profile, at least a portion of which that is obliquely angled with respect to a plane of the metallic plate.

In another variant, the electrical connector is further adapted to be dislodged from the received sensor at a force which is adjustable via incorporation of one or more modifiable components and the modification comprises changing the shape or cross-sectional profile of at least one of the one or more modifiable components.

In a fourth embodiment, the electrical connector is used in biomedical applications having at least two terminals each with different diameters, and the connector comprises: first and second body elements pivotally mated to one another; and a variable-geometry aperture, the geometry of the aperture being controlled at least in part by pivoting of the first and second body elements; wherein the variable-geometry aperture is configured to: allow a first of the terminals having a first diameter to be received within the aperture; and prevent a second of the terminals having a second diameter to be received within the aperture; wherein the first diameter is smaller than the second diameter.

In one variant, the first terminal comprises an ICG (impedance cardiography) terminal, and the second terminal comprises an ECG (electrocardiography) terminal.

In another variant, the first diameter comprises 0.125 in., and the second diameter comprises 0.155 in.

In a fifth embodiment, the electrical connector is used in biomedical applications having at least two terminals each with different diameters, and the connector comprises: first and second body elements pivotally mated to one another; and a variable-geometry aperture, the geometry of the aperture being controlled at least in part by pivoting of the first and second body elements; wherein the variable-geometry aperture is configured to: allow a first of the terminals having a first diameter to be received within the aperture; and prevent a second of the terminals having a second diameter to be securely grasped within the aperture; wherein the first diameter is larger than the second diameter.

In one variant, the first terminal comprises an ICG (impedance cardiography) terminal, and the second terminal comprises an ECG (electrocardiography) terminal.

In another embodiment the first diameter comprises 0.185 in., and the second diameter comprises 0.155 in.

In still another variant, the prevention of the second of the terminals having a second diameter to be securely grasped within the aperture is provided at least in part by a stop apparatus, the stop apparatus limiting the travel of the first and second body elements relative to one another.

In another embodiment, the connector apparatus comprises: a first movable actuation element having an electrically conductive element associated therewith, a second movable actuation element having at least one feature for receiving an upper portion of a sensor, wherein the first moveable actuation element is adapted to receive at least a portion of the second moveable actuation element and wherein the mating forms an aperture adapted to receive at least an upper portion of the sensor, and a pivoting element adapted to mechanically attach the first and second movable actuation elements such that they are adapted to pivot with respect to one another, wherein upon biasing at least one of said first and second movable actuation elements, the aperture expands in size, and wherein upon unbiasing the at least one movable actuation elements, the aperture contracts in size due at least in part to spring force generated by the pivoting element.

In one variant, at least one of the first or second actuation elements comprises a metal contact portion, the metal contact portion being adapted to encircle at least a portion of a received sensor.

In another variant, the connector is adapted to receive a 0.0125 in. sensor. Accordingly, the aperture of the connector is unable to accommodate at least an upper portion of a sensor of larger size. In yet another embodiment, the connector is adapted to receive a 0.0185 in. sensor. Accordingly, the aperture of the connector is able to accommodate at least an upper portion of a sensor of smaller size, however is unable to lock such a sensor into the connector via one or more mechanisms for locking.

In another variant, the pivoting element comprises a spring-loaded pivot which rests in a closed position and is permanently attached to the connector.

In a second aspect of the invention, a method of manufacturing an electrical connector is disclosed. In one embodiment, the electrical connector has a plurality of components, the connector being adjustable with respect to at least one physical attribute without requiring a tooling change, and the method comprises: providing tooling for a portion of the components; forming the portion of the components using the tooling; providing others of the components; adjusting one or more of the others of the components so as to achieve a desired physical attribute; and assembling the components to form the connector.

In one variant, the connector is adapted for use in a biomedical application, the desired physical attribute comprises pull-away force, and the adjusting comprises modifying the shape of the one or more other components and wherein the biomedical application comprises an ICG terminal.

In another variant, the connector is adapted for use on an ICG sensor terminal, the desired physical attribute comprises pull-away force, and the adjusting comprises: modifying the shape of the one or more other components in contact with the sensor terminal; and adjusting the tension of a spring, the spring being used to maintain the connector substantially clamped onto the terminal.

In still another variant, modifying the shape of the one or more other components comprises modifying the cross-sectional shape of at least a portion of a contact region of an electrical contact element, the contact region being in contact with a sensor terminal.

In another embodiment, the method comprises: providing a metal contact plate; forming a first actuator element; disposing said metal contact plate within the first actuator element; forming a second actuator element; mating the first actuator element and the second actuator element; disposing a spring-loaded pivoting element within the mated first and second actuator elements; and mechanically and electrically testing the connector. In another embodiment, a second metal contact plate is disposed in the second actuator element. In yet another embodiment, the acts of mechanically and electrically testing the connector comprise mating the connector to a terminal or other electrically conductive device and performing electrical continuity or resistance testing thereof. In another embodiment, the acts of mechanically and electrically testing the connector comprise testing for voltage withstand or other electrical, mechanical or insulating properties.

In a third aspect of the invention, an improved method of operating a biomedical connector is disclosed. In one embodiment, the method comprises: disposing a biomedical sensor in a desired location on a subject; coupling the connector to the sensor, the coupling comprising capturing a sensor terminal within a substantially V-shaped aperture and a notch of the connector using spring tension; passing at least one electrical signal through the sensor and connector; and removing the connector from the sensor. In one variant, coupling the connector comprises receiving and capturing only an appropriately sized sensor terminal within the connector aperture.

In a fourth aspect of the invention, a biomedical evaluation system is disclosed using the aforementioned connector(s). In one embodiment, the system comprises an impedance cardiography (ICG) device adapted to use the connectors to electrically connect the system to patch-type electrodes disposed on the thorax of the subject being evaluated. In one variant, the signals to and from the various electrodes are passed from and to the system, respectively via a ganged cable element having a plurality of conductors and associated connectors at their distal ends.

In a fifth aspect of the invention, a method of preventing erroneous readings from a living subject is disclosed. In one embodiment, the method comprises: placing first, second, and third terminals on a subject, said terminals having first, second and third sizes respectively, each of said sizes being different than the others; providing first, second and third electrical connectors, said first and third electrical connectors being adapted to receive and securely mate with only said first and third sizes of terminals, respectively; and placing said first, second and third connectors on respective ones of said first, second and third terminals.

In one variant, the first terminal comprises a (small) ICG terminal, the second terminal an ECG terminal, and the third terminal a (large) ICG terminal.

BRIEF DESCRIPTION OF THE DRAWINGS

The features, objectives, and advantages of the invention will become more apparent from the detailed description set forth below when taken in conjunction with the drawings, wherein:

FIG. 2b illustrates a resistor of the type located within the body portion of the connector apparatus of FIG. 2a.

FIGS. 2l-2m are bottom and top view perspective views, respectively, of the finger portion of the connector of FIG. 2a.

FIGS. 2n-2o are side views of the finger cradle of the body portion of the connector of FIG. 2a.

FIGS. 2q-2r are top and cross-sectional views of exemplary metal contact plates useful in the connector of FIG. 2a.

FIG. 2s is a cross-sectional view of an exemplary pivot pin configuration, illustrating its asymmetric attributes and interference fit within the connector of FIG. 2a.

FIGS. 3l-3m are bottom and top view perspective views, respectively, of the finger portion of the connector of FIG. 3a.

FIG. 4 is a block diagram illustrating an exemplary method of manufacturing a large or small sensor accepting connector of the present invention.

FIG. 5 is a block diagram illustrating an exemplary method of using a large or small sensor accepting connector according to the present invention.

Figure 1:
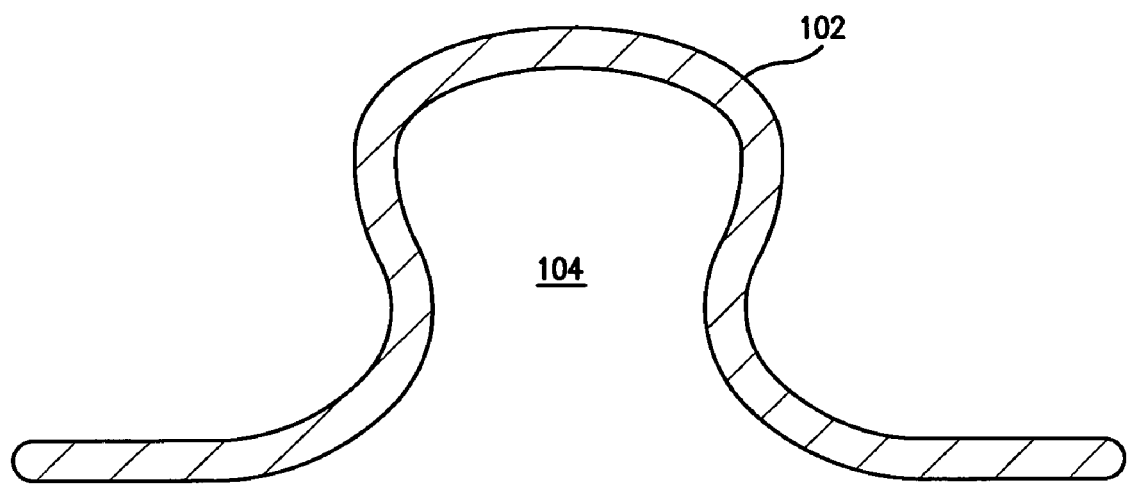
FIG. 1 is a cross-sectional view of an exemplary sensor for use with the connector of the present invention.

All figures © Copyright 2008 CardioDynamics International Corporation. All rights reserved.

DETAILED DESCRIPTION OF THE INVENTION

Reference is now made to the drawings wherein like numerals refer to like parts throughout.

As used herein, the terms "user", "caregiver", and "clinician" are used interchangeably to refer to a person positioning, using, actuating, or removing the connector or associated components, or practicing the methods disclosed herein, whether for monitoring or treatment of another subject or themselves.

As used herein, the term "biomedical" includes any application for which the transfer of an electrical current or potential is useful in providing treatment or otherwise assessing a biological subject, including without limitation impedance cardiography (ICG), electrocardiography (ECG), and electroencephalography.

As used herein, the terms "subject" "patient" and "living subject" refer not only to human beings, but also any other species which may benefit from biomedical analysis, evaluation or treatment.

It will be appreciated that the terms "upper", "lower", "top", "bottom", "front", "rear", and the like are used herein generally to describe position with respect to other components of the invention or associated structures, as opposed to connoting any sort of absolute position, location or relationship. For example, a "lower" housing element may actually be above the "upper" housing element when the connector is installed in an inverted orientation.

Overview—

In one salient aspect, the present invention provides an improved connector apparatus for use in biomedical applications such as ICG or ECG monitoring. This connector is optimized for specificity of use with a single sized sensor, and high electrical performance. In one exemplary embodiment, the connector comprises a two piece actuator assembly (a body and a finger) which when mated create an aperture for receiving a sensor. The connector aperture is specifically designed to frustrate receipt of sensors (i.e., their terminals) which are larger than the intended terminal, and to be unable to lock into place sensor terminals which are smaller than the intended size (thereby frustrating electrical continuity at very least). The connector allows for visibility of the receipt of the sensor into the connector so as to be easy for a clinician to use, and firmly engages (or locks) a particularly sized and shaped sensor (e.g., a "button" type) into contact with the connector when closed. The foregoing functionality is important for example in ICG/ECG monitoring, wherein different sized sensor terminals are utilized, and connection of an ICG lead to an ECG sensor (or vice versa) is highly undesirable. Hence, the exemplary embodiments of the connector described herein are "two way" protective; i.e., (i) a connector adapted for ECG use cannot be mated to an ICG terminal, and (ii) a connector adapted for ICG use cannot be mated to an ECG terminal.

In one variant, a "small" sized connector that can be clamped onto a "small" ICG terminal (i.e., 0.125 in. diameter) but will not receive a larger (i.e., 0.155 in.) ECG terminal is provided. In another variant, a "large" sized connector that can receive and be clamped onto the large ICG terminal (i.e., 01.85 in.), but will not clamp onto or grasp the smaller ECG (0.155 in.) terminal (or the small ICG terminal).

The connector actuator elements (body and finger) are pivotally connected to one another. In one embodiment, the pivot comprises a spring-loaded pivot having no external stops. Rather, the shape of the aperture and stops are defined by a metal insert associated with the body element and the pivot is formed within the connector so as to require effectively the destruction of the connector for access thereto. Thus, a user is effectively prevented from changing the properties of the connector to accept smaller or larger sensors.

The particular pull-away attributes of the connector may also be "tuned" to given the physical properties such as shape, etc. of the metal insert associated with the body element and/or of the overall connector itself.

Methods of manufacture and use are also disclosed. In one variant, the design of the connector and the associated method of manufacture are such that the aforementioned pull-away (force) is tunable without having to re-tool the connector; i.e., one or more components of the connector can be adjusted to effect the desired pull-away force without having to modify the tooling.

DETAILED DESCRIPTION OF THE EXEMPLARY EMBODIMENTS

As noted above, ICG sensors are disposed on a patient in order to transmit and detect electrical and impedance changes in the thorax. Hemodynamic parameters are calculated using the impedance measurements. As noted, at least one sensor is used for transmitting electrical current through the chest, and at least one other sensor is used to detect or sense voltage. These sensors are different sizes in order to facilitate coupling of the connectors to the appropriate sensor.

Exemplary sensors are disclosed in co-owned U.S. Pat. No. 7,270,580 issued Sep. 18, 2007 and entitled "Methods and Apparatus for Conducting Electrical Current", which is incorporated by reference in its entirety. As discussed in greater detail therein, and as illustrated in FIG. 1, sensors 100 generally comprise a head or cap 102, a shaft 104, and a base 106. The base 106 is placed into contact with the surface of the skin of a patient (not shown); and the shaft 104 extends from the base 106 and terminates at the cap 102.

It will be appreciated that while described herein primarily in terms of a connector apparatus adapted for biomedical applications such as ICG, the connector may also readily be adapted to other applications, whether biomedical (such as ECG) or otherwise. Likewise, the various embodiments of the connectors described herein may be used in conjunction with the technology and/or sensors described in the following co-owned U.S. patents: U.S. Pat. No. 7,251,524, issued Jul. 31, 2007 to Hepp, et al., and entitled "Apparatus and method for determining cardiac output in a living subject"; U.S. Pat. No. 7,214,107 issued May 8, 2007 to Powell, et al., and entitled "Electrical connector apparatus and methods"; U.S. Pat. No. 7,149,576 issued Dec. 12, 2006 to Baura, et al., and entitled "Apparatus and method for defibrillation of a living subject"; U.S. Pat. No. 7,043,293 issued May 9, 2006 to Baura and entitled "Method and apparatus for waveform assessment"; U.S. Pat. No. 6,636,754 issued Oct. 21, 2003 to Baura, et al., and entitled "Apparatus and method for determining cardiac output in a living subject"; U.S. Pat. No. 6,602,201 issued Aug. 5, 2003 to Hepp, et al., and entitled "Apparatus and method for determining cardiac output in a living subject" (describing, inter alia, predetermined terminal spacing); U.S. Pat. No. 6,561,986 issued May 13, 2003 to Baura, et al., and entitled "Method and apparatus for hemodynamic assessment including fiducial point detection"; and the following co-owned, co-pending U.S. patent applications: U.S. patent application Ser. No. 10/453,820 filed Jun. 2, 2003 and entitled "Physiologic stimulator tuning apparatus and method" and U.S. patent application Ser. No. 10/995,920 filed Nov. 22, 2004 and entitled "Method and apparatus for signal assessment including event rejection", each of the foregoing being incorporated herein by reference in its entirety. All such adaptations and alternate embodiments will be readily understood by those of ordinary skill given the present disclosure, and are considered to fall within the scope of the claims appended hereto.

It is also noted that while the invention is described as having "large" and "small" sensor-accepting embodiments, these are merely relative terms, and alternatively sized embodiments may readily be substituted. Furthermore, to the extent the features are compatible with a particular connector, the various features described herein are intended to be representative and descriptive of each of the available embodiments.

"Small" Sensor Accepting Connector Apparatus—

Figure 2A:
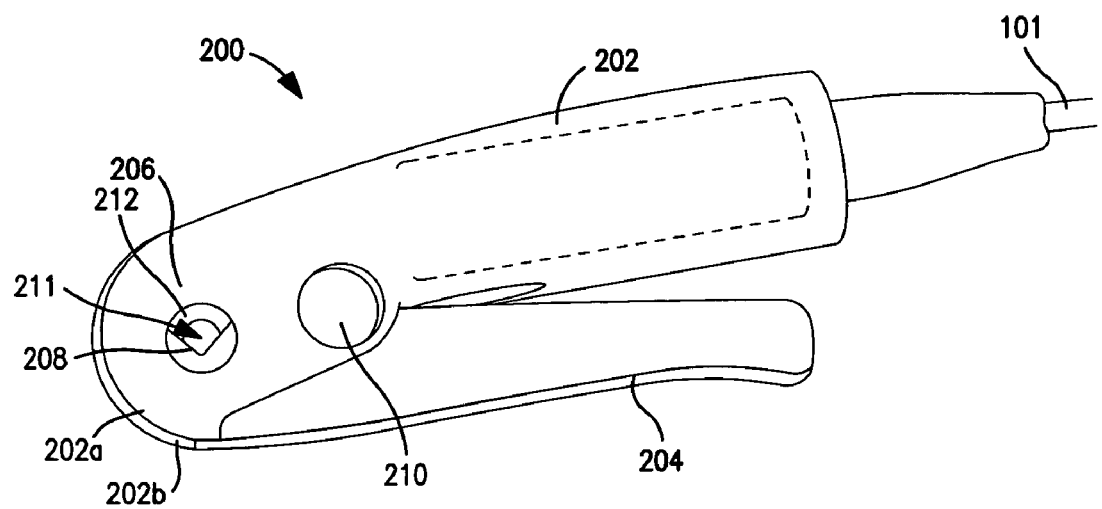
FIG. 2a is a top perspective view of an exemplary embodiment of a small sensor accepting connector apparatus of the present invention.
Figure 2B:
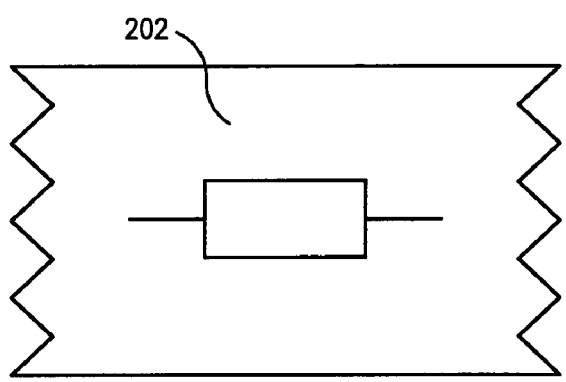
Figure 2C:
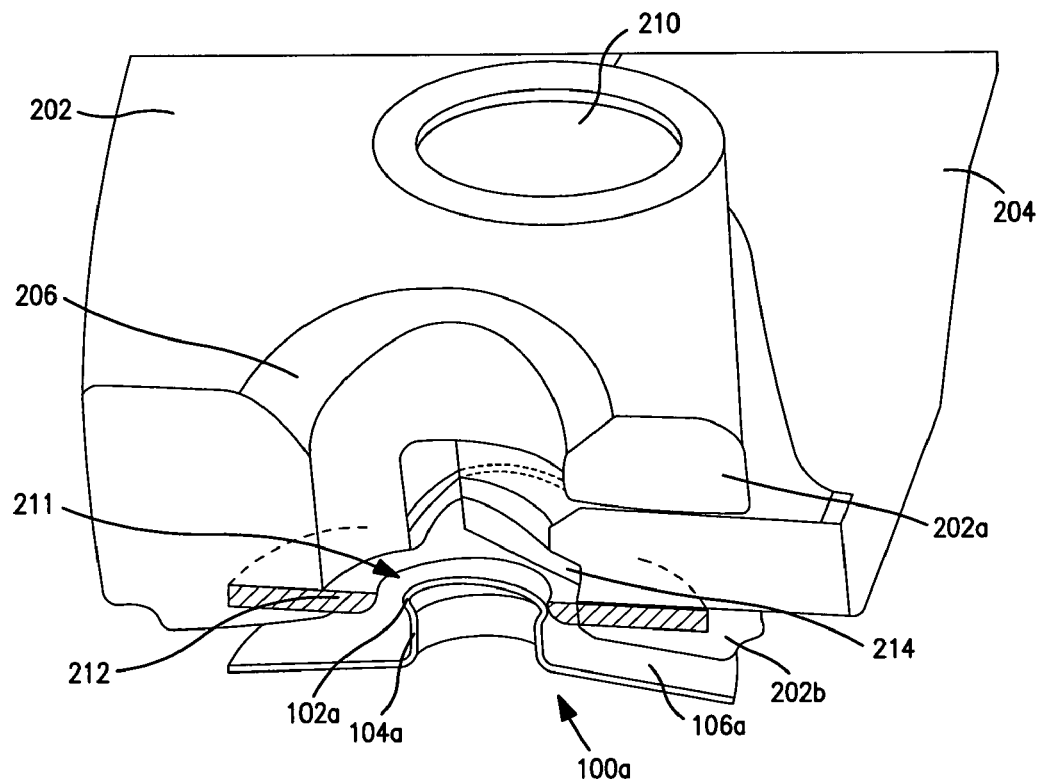
FIG. 2c is cross-sectional view of the connector of FIG. 2a in the open position and having a small sensor accepted.
Figure 2D:
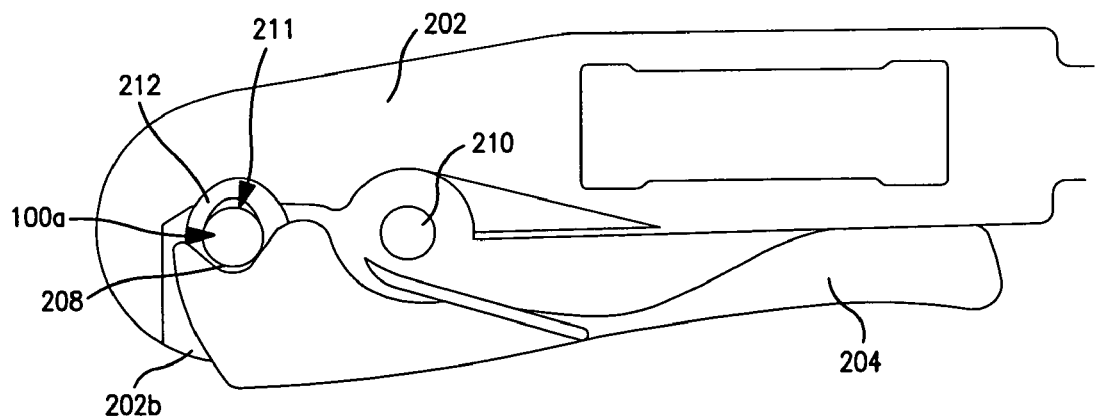
FIG. 2d is a top perspective view of the connector of FIG. 2a in the open position and having the bottom platform layer exposed, the top platform layer removed, and having a small sensor accepted.
Figure 2E:
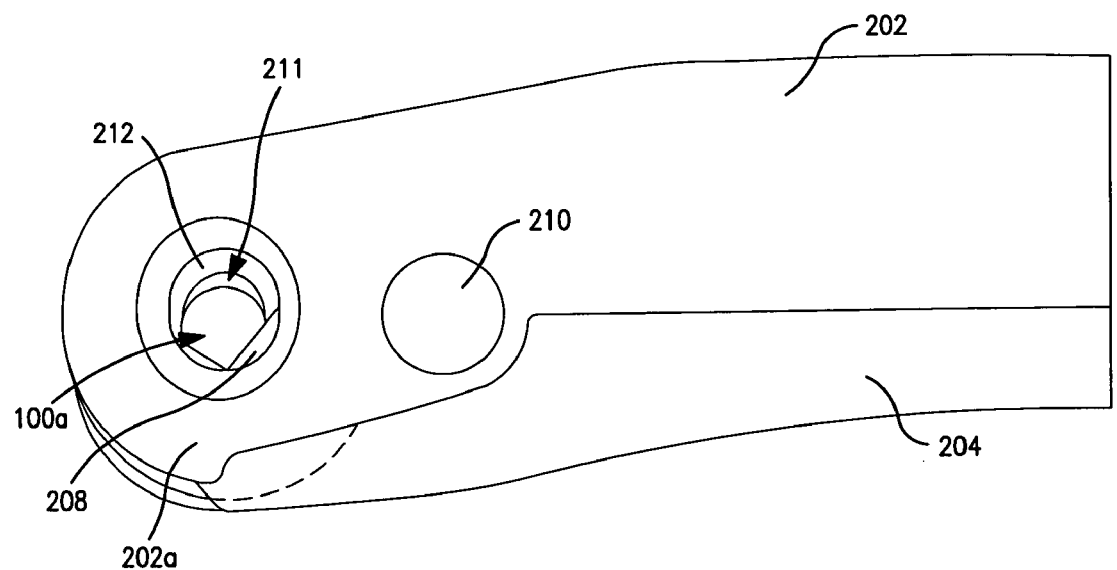
FIG. 2e is a top perspective view of the connector of FIG. 2a in the open position and having the bottom platform layer removed and having a small sensor accepted.
Figure 2F:
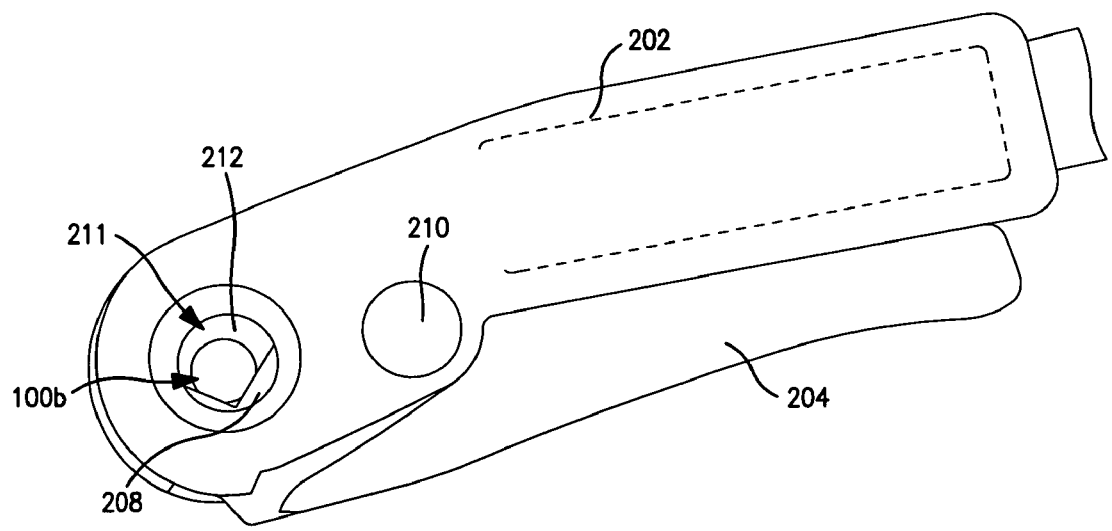
FIG. 2f is a top perspective view of the connector of FIG. 2a in the open position and illustrating the connector's inability to accept a large sensor.
Figure 2G:
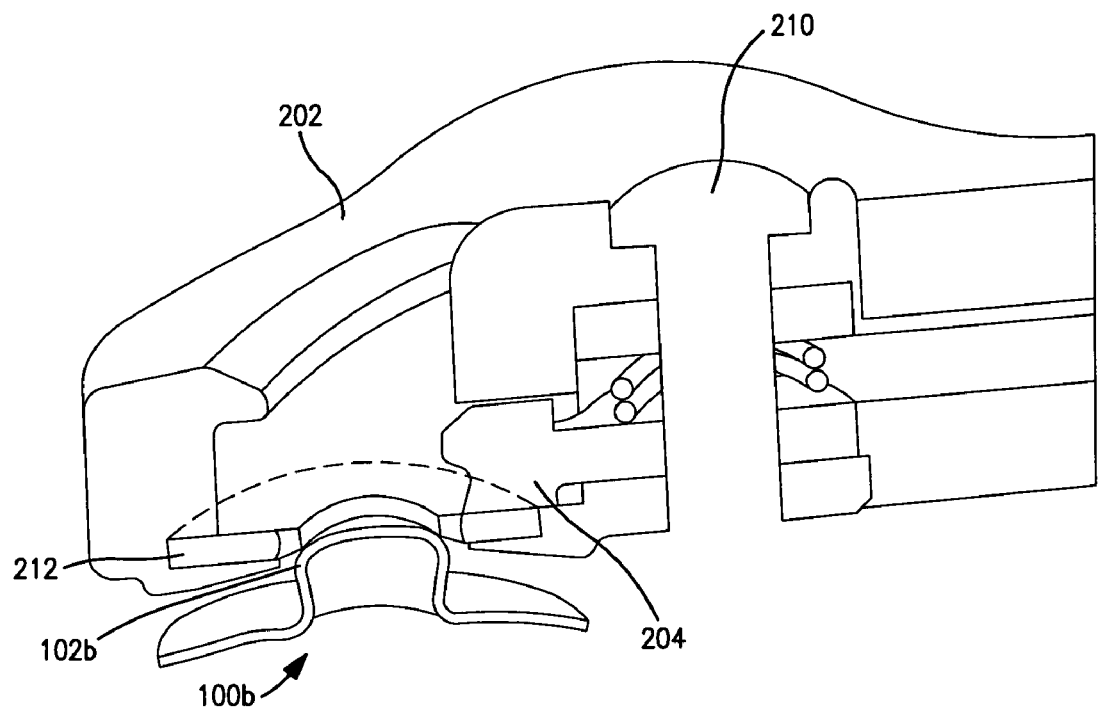
FIG. 2g is a cross-sectional view of the connector of FIG. 2a in the open position and illustrating the connector's inability to accept a large sensor.
Figure 2H:
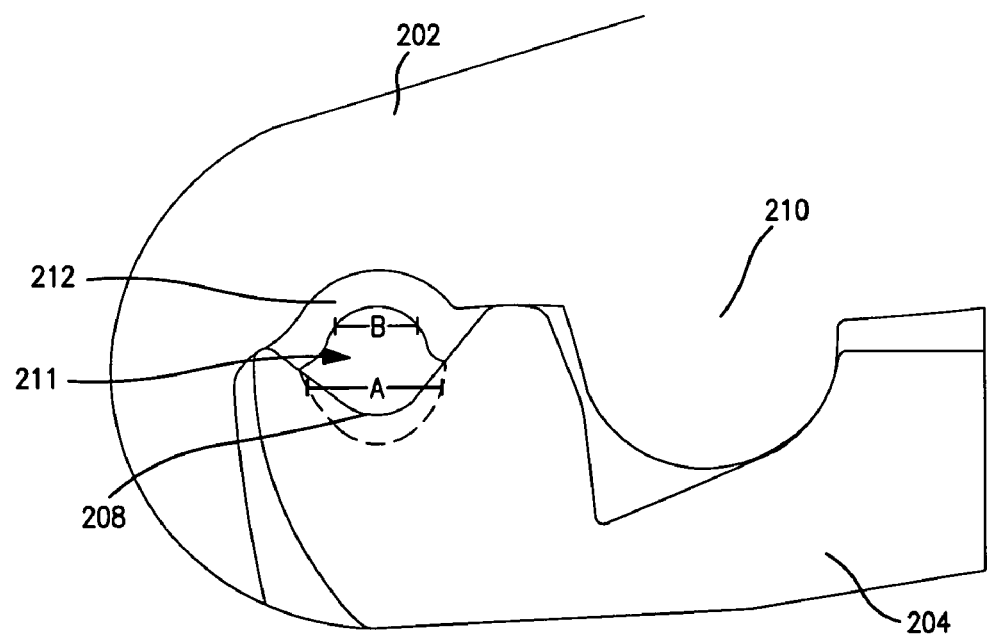
FIG. 2h is a top view of the connector of FIG. 2a in a closed position having the top platform layer removed.
Figure 2I:
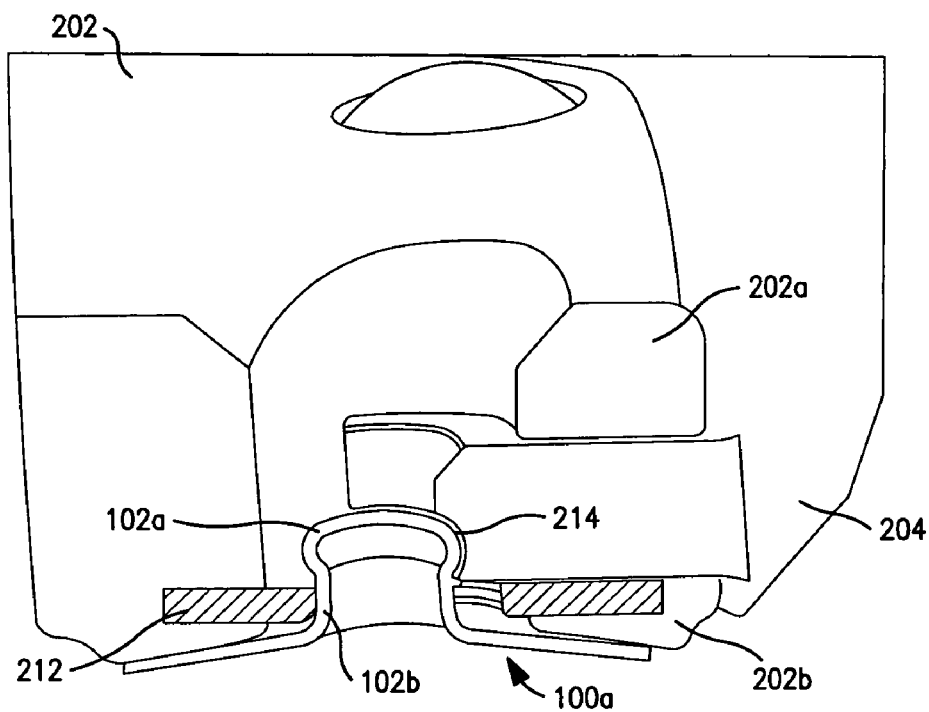
FIGS. 2i-2j are cross-sectional views of the connector of FIG. 2a in the closed position and illustrating the mating of a small sensor within the connector.
Figure 2J:
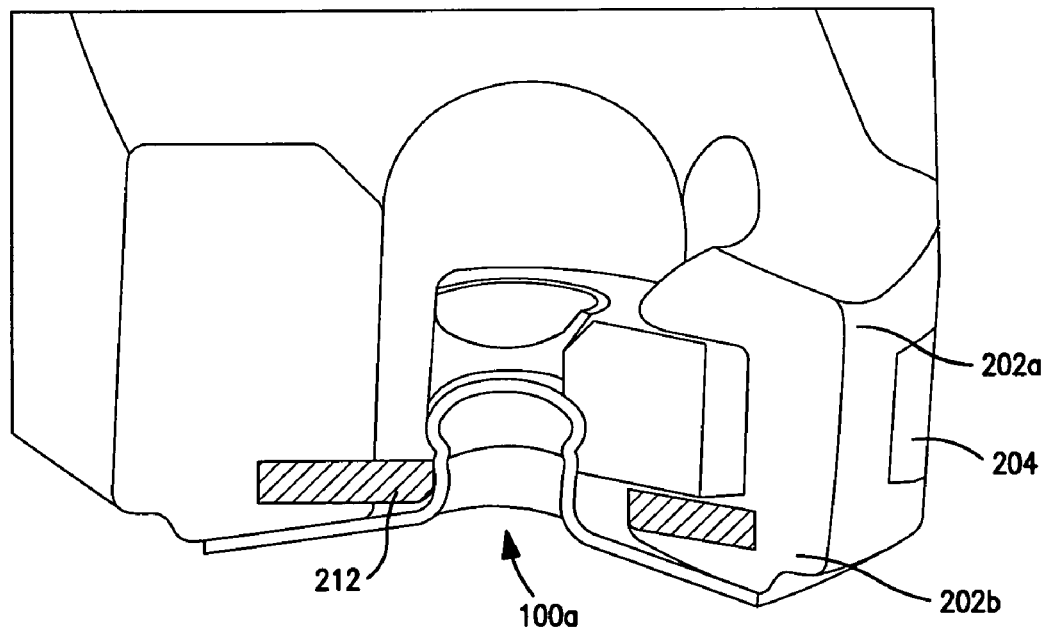
Figure 2K:
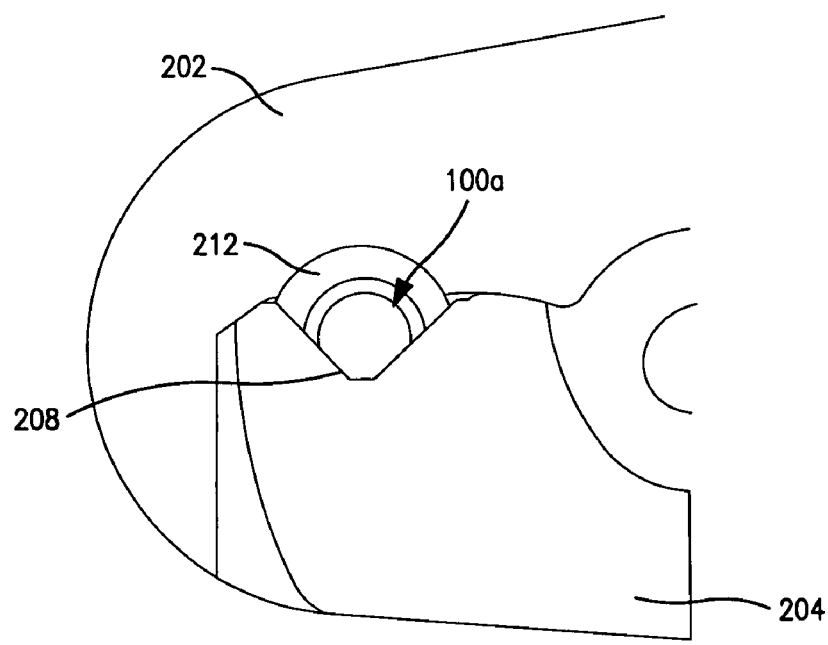
FIG. 2k is a top view of the connector of FIG. 2a in the closed position and having the top platform layer removed and having a small sensor accepted.
Figure 2L:
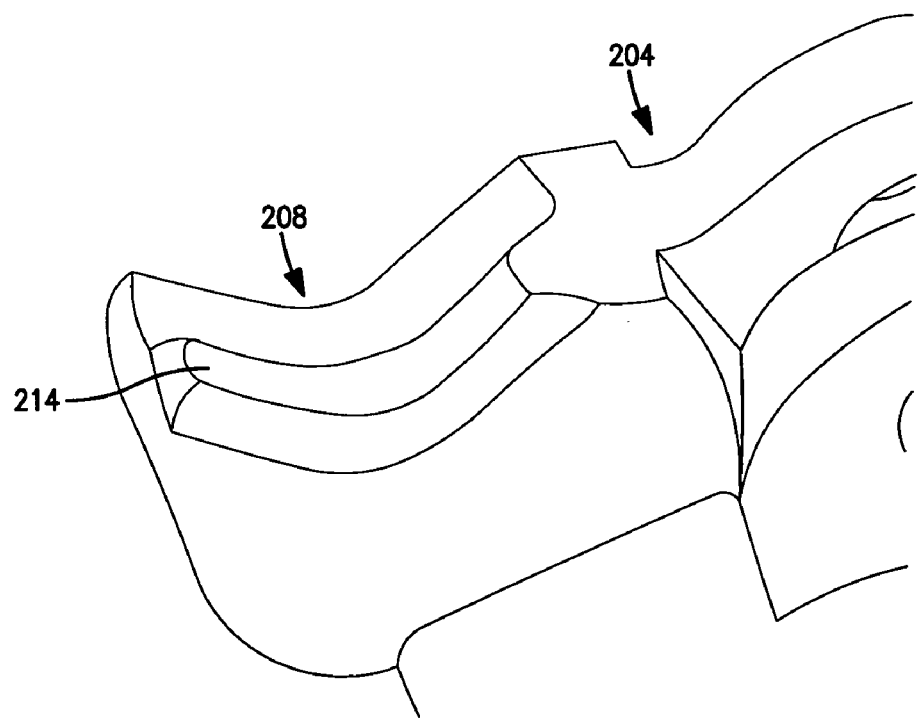
Figure 2M:
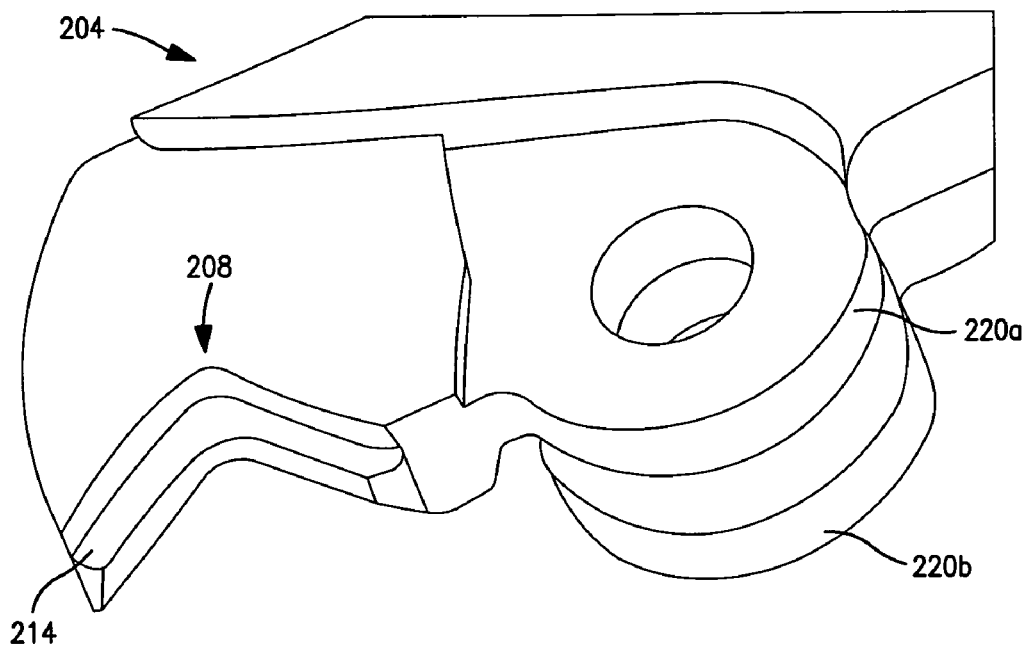
Figure 2N:
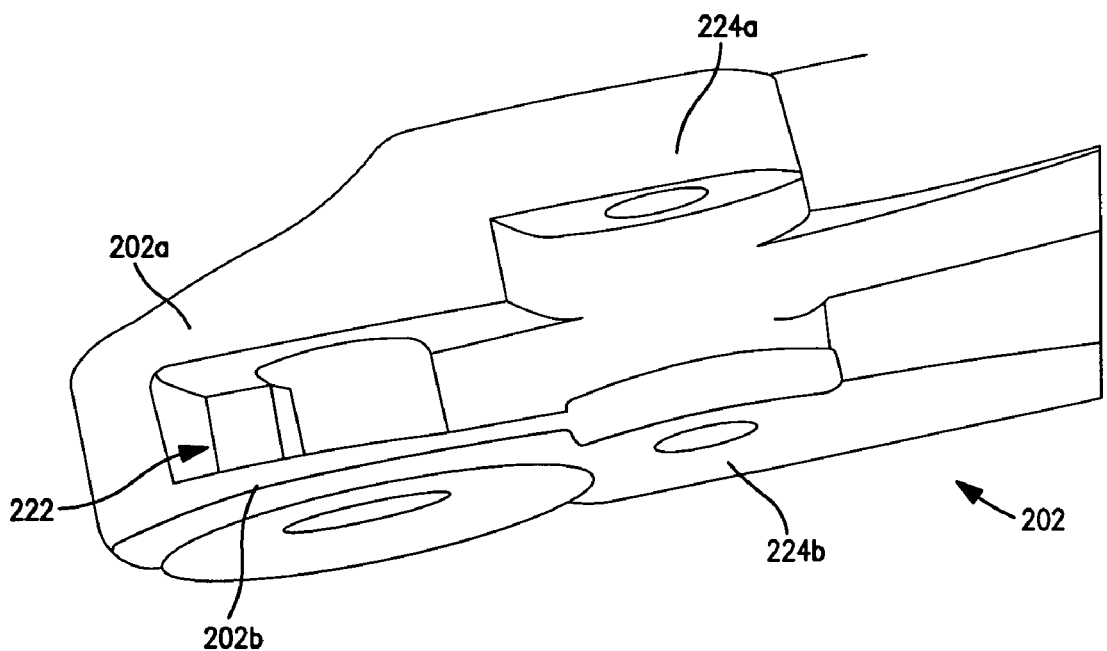
Figure 2O:
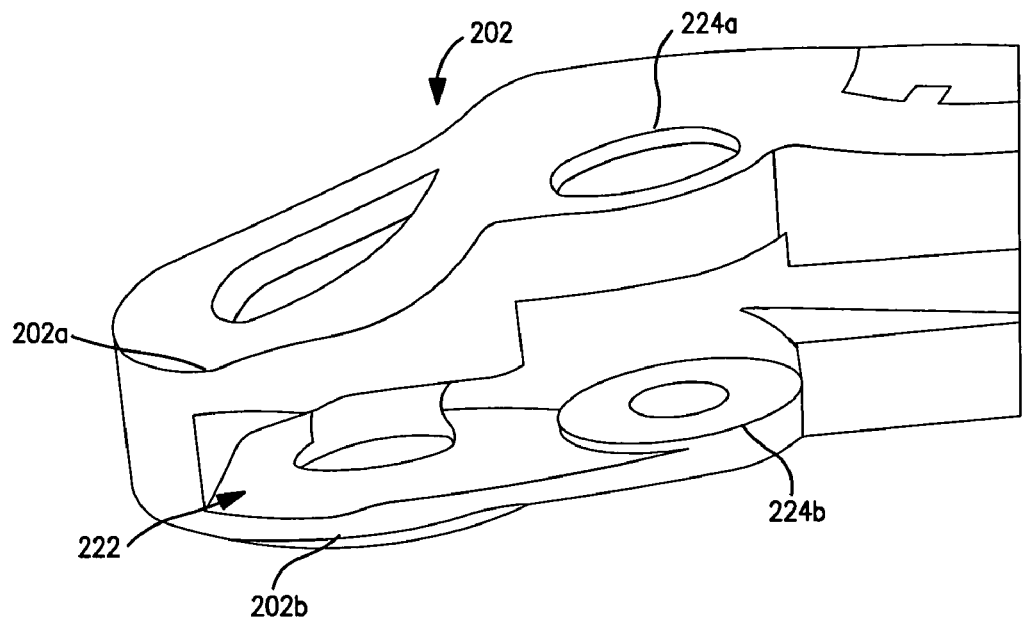
Figure 2P:
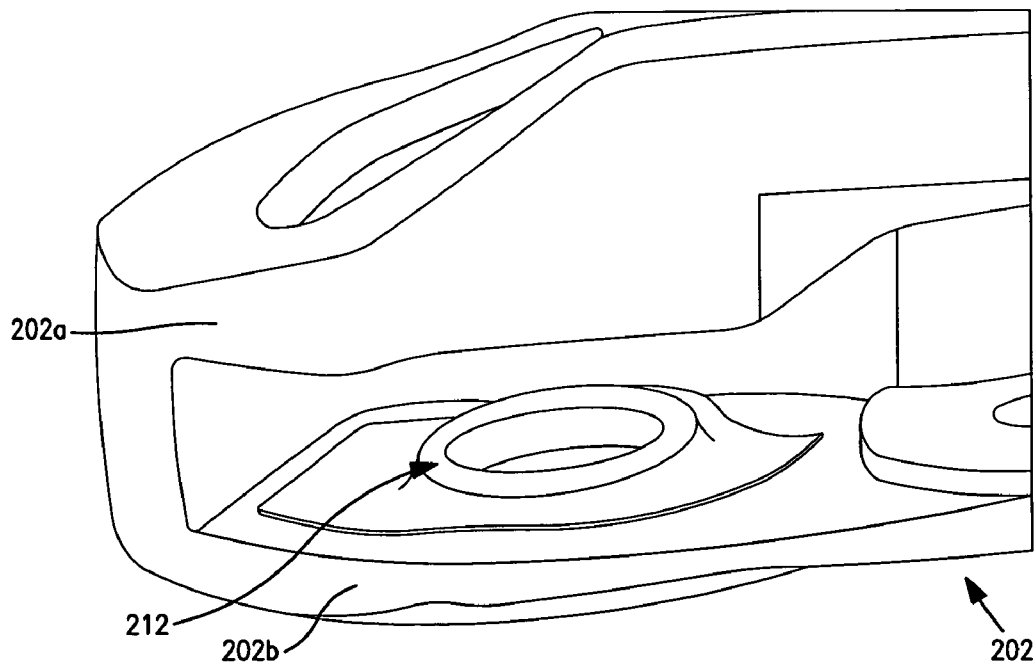
FIG. 2p is a side view of the body portion of the connector of FIG. 2a illustrating the metal contact plate.

Referring now to FIGS. 2a-2p, an exemplary embodiment of a connector apparatus of the present invention is described.

As shown in FIG. 2a, the exemplary connector apparatus 200 generally comprises two actuators, a connector body 202 and a finger 204. The connector body 202 has an electrical cable 201 issuing generally from one end thereof. The cable 201 provides the electrical interface between the connector 200 and an external system (e.g., ICG or ECG monitoring system, not shown).

The connector body 202 and finger 204 comprise a molded polymer such as ABS (acrylonitrile butadine styrene), although other materials such as polyethylene, fluoropolymers (e.g., ETFE), and the like may be used. ABS is selected in the illustrated embodiment for its comparatively high strength and other excellent mechanical properties, as well as comparatively low cost and ease of handling.

These components 202, 204 rotate about a fixed pivot 210 which acts as a fulcrum and, when mated, the body 202 and finger 204 form a sensor accepting aperture 211. The aperture 211 takes a shape defined by a metal contact plate 212 associated with the body 202 and the v-shaped stop 208 of the finger 204. (The metal contact plate 212 will be discussed in greater detail below.) The body 202 also includes a chamfered or beveled dimple 206 which is chamfered inward toward the aperture 211 so as to inter alia provide optimum visibility at all angles when a user or clinician is placing the connector 200 on a sensor 100.

The body 202 may also include one or more resistors (or other electrical or electronic components) inside the portion of the body 202 nearest the electrical cable 201, as illustrated in FIG. 2b. These resistors are used to provide for example dissipation of defibrillation or other energy (high voltage) which may pass through the connector when the ICG system (or at least the terminals and leads thereof) is left on a patient and the patient is defibrillated. In this manner, the connector may advantageously remain connected to the patient without potential for causing damage to the equipment due to this high voltage. In one embodiment, the resistor is selected so that the dissipation of energy does not exceed 10% of the applied defibrillation energy, so as to comply with ANSI/AAMI EC 53-1995 Standards. However, alternative embodiments including those dissipating more or less energy are recognized by the inventors hereof.

It is further noted that, although the illustrated embodiment shows the resistors disposed within the body 202 of the device, the resistors may alternatively be located within a parent device (e.g., an ICG "yoke" of the type described in the previously referenced patents incorporated herein), or within the connector cable as well, although this may not provide compliance with the aforementioned EC 53-1995 or other Standard(s).

Further, the resistors may be of fixed or variable resistance in nature, may include four or five-band axial resistors, and may be placed in parallel or in series, as is well known to those of ordinary skill in the electrical arts.

Referring now to FIG. 2c, a cross-sectional view of the receipt of a "small" sized sensor terminal 100a within the aperture 211 is illustrated. Although the illustrated connector 200 is particularly adapted to receive a sensor terminal 100a having a 0.125 in. diameter head 102a or "cap", it is appreciated the connector 100 may be uniquely adapted to receive sensor terminals 100 having heads with other diameters as well. The connector 200 of FIG. 2c is illustrated in the open position thus enabling a user to place the connector 200 over the 0.125 in. sensor 100a such that the sensor's cap 102a is received within the aperture 211 formed by the metal contact plate 212 and finger 204. The finger 204 of the illustrated embodiment includes a grooved interior surface 214. The grooved surface 214 is particularly adapted to match the protrusions of the sensor cap 102a. Thus, when the sensor 100a is inserted into the aperture 211, the cap 102a rests snugly within the groove 214 of the finger 204.

FIG. 2c also illustrates the connector body 202 of the exemplary connector 200 composed of top 102a and bottom 102b platforms, the platforms 102a, 102b (as will be discussed in greater detail below) are disposed with respect to one another in such a manner so as to create a "cradle" within which the finger 104 is at least partially disposed.

FIG. 2d is a top perspective view of the connector of FIG. 2a. The connector 200 is illustrated in the open position with a small sensor terminal 100a accepted in the aperture 211. FIG. 2d depicts finger 204 resting above the bottom platform 202b; the top platform 202a has been removed. As noted previously, the finger 204 comprises a V-shaped stop 208 which moves away from the center of the aperture 211 when the connector 200 is opened, thereby allowing the cap 102 of the sensor terminal 100 to pass through the aperture 211 opening.

FIG. 2e shows the connector 200 having the top platform 202a disposed atop the finger 204 while the connector is in the open position and a small sensor terminal 100a is received.

FIGS. 2f and 2g illustrates the mechanism by which the exemplary connector 200 adapted for receiving small sensor terminals 100a is unable to receive a sensor 100 having a head or cap with a diameter larger than that which it is adapted to receive. In the illustrated embodiment, the connector is adapted to receive a sensor 100a having a head 102a with a diameter of 0.125 in. The "large" sensor in this illustration has a head 102b with a diameter of 0.155 in., however it is appreciated that this diameter is merely exemplary and that the described concepts are equally applicable to any sensor terminal 100 having a head with a diameter larger than the diameter which the connector 200 of the present invention is particularly adapted to receive.

As is most clearly demonstrated in FIG. 2g, when a user places the connector 200 in open position, i.e., when the V-shaped stop 208 of the finger is moved away from the center of the aperture 211 to permit entry of the cap 102 of a sensor terminal 100, the aperture opening is too small for the cap 102b of the larger sensor terminal 100b to fit within. Therefore, a user is unable to cause the smaller-sensor accepting connector 200 to receive a connector other than that which the connector 200 is particularly adapted to fit. This functionality is particularly advantageous in the biomedical (e.g., ICG/ECG) context, since connectors cannot be inadvertently (or intentionally) placed on the wrong terminals.

Referring now to FIG. 2h, the exemplary small sensor accepting connector 200 is illustrated in the closed position. As shown, the aperture 211 of the connector 200 is particularly shaped ("eccentric") so as to have two sections, the first section has a first diameter A, which is larger than the diameter B of the second section. The first diameter A is sized according to the size of the cap 102 of the sensor 100 which will be received by the connector 200. In the illustrated example, the connector 200 is adapted to receive a sensor 100a having a head 102a with a diameter of 0.125 in., thus the first diameter A of the aperture 211 must be adapted to accommodate at least 0.125 in. The second diameter B is sized generally according to the size of the shaft 104 of the sensor 100 which will be received by the connector 200. In this manner, when the terminal head is passed through the larger diameter portion of the aperture (such that the shaft portion is in the plane of the metal contact plate and V-shaped stop 208), then the V-shaped stop 208 engages the shaft of the terminal when the connector is closed, pushing the shaft laterally into the narrower portion of the aperture (diameter B) which is in the illustrated embodiment contoured approximately to the shape of the terminal shaft, thereby capturing the shaft more securely and providing enhanced electrical contact area.

FIG. 2h also illustrates the V-shaped stop 208 of the finger element 204. When the connector 200 is in the open position, the stop 208 is moved away from the center of the aperture 211 thus creating an aperture large enough to receive the cap portion 102 of an appropriately sized sensor 100. When the connector 200 is closed, the stop 208 is adapted to push the shaft 104 of a sensor 100 into the smaller diameter section B of the aperture 211 as previously described. The sensor 100 is then locked into the connector 200 because, when the connector 200 is closed, the aperture is no longer large enough to accommodate the sensor terminal cap 102. The two tips of the V-shaped stop 208 are abutted against the interior walls of the body 202 when the connector 200 is fully closed.

It will be recognized that while a V-shaped component 208 is used, other shapes may feasibly be used consistent with the invention in order to both firmly contact and hold the terminal boy within the connector, and preclude entry of the wrong-sized terminal.

FIGS. 2i and 2j demonstrate the exemplary "small" sensor accepting connector 200 in the closed position and having a small sensor 100a locked into place. As illustrated, when the connector 200 is closed, the small sensor 100a is unable to disengage, as it is held in place by the metal contact plate 212 and groove 214. The metal contact plate 212 and the V-shaped stop 208 maintain a smaller aperture 211 when closed. Specifically, the metal contact plate 212 disposed under the cap 102a at the shaft 104a of the sensor 100a and grooved 214 finger pushes against the cap 102a toward the body 202. Because the shaft 104a has a smaller diameter than the cap 102a, the sensor 100a is prevented from egress through the aperture 211 (by which it entered the connector 200).

Referring now to FIG. 2k, the exemplary small sensor accepting connector 200 is illustrated having a small sensor 100a locked in place. As illustrated, the sensor 100a is held against the metal contact plate 212 by the finger 204 exerting a force in the direction of the body 202. The cap 102a is disposed above the metal contact plate 212 and portions of it are received within the grooved portion 214 of the finger 204.

The finger 204 is illustrated in greater detail in FIGS. 2l-2m. As shown, the finger 208 has a generally V-shaped stop 208 which accommodates the cap 102 of a sensor terminal 100, and has a grooved feature 214 for maintaining the cap 102. The finger 204 also comprises first and second pivot rings 220 which are disposed about the pivot 210 and enable the finger to rotate toward and away from the body 202.

FIGS. 2n-2p illustrate the portions of the connector body 202 which form the "cradle" 222 within which the finger 204 is disposed. As noted above, the cradle 222 is formed by the upper 202a and lower 202b platforms of the body 202. The upper 202a and lower 202b platforms also comprise upper and lower pivot receiving apertures 224a and 224b, respectively, which receive the pivot 210 when the finger is mated therein.

The pivot 210 of the illustrated embodiment generally comprises a spring-loaded pivot 210 having no external stops. Because there are no external stops, a user may not adjust the opening or aperture 211 of the connector 200. Rather, the aperture 211 is defined by the metal contact plate 212 and V-shaped portion 208 only and may not be made larger or smaller. The spring-loaded pivot 210 rests in a closed position. In other words, in the closed position, the V-shaped stop 208 of the finger 204 abuts the interior walls of the body 202 (as demonstrated in FIG. 2h). Force must be applied to the end of the finger 204 nearest the electrical cable 101 in the direction of the connector body in order to cause the V-shaped stop 208 portion of the finger 204 to move away from the body 202 (i.e., put the connector 200 in an open position, as demonstrated in FIG. 2e). When force is no longer applied, a spring in the pivot 210 will cause the connector 200 to return to the closed position. In the illustrated embodiment, the spring-loaded pivot 210 is placed within the connector 200 permanently. Permanent placement substantially frustrates a user from changing the stopping properties of the pivot (e.g., to cause the connector to accept and/or lock into place larger or smaller sensor terminals) because, in order to access the pivot 210, the entire connector must be effectively destroyed.

Figure 2Q:
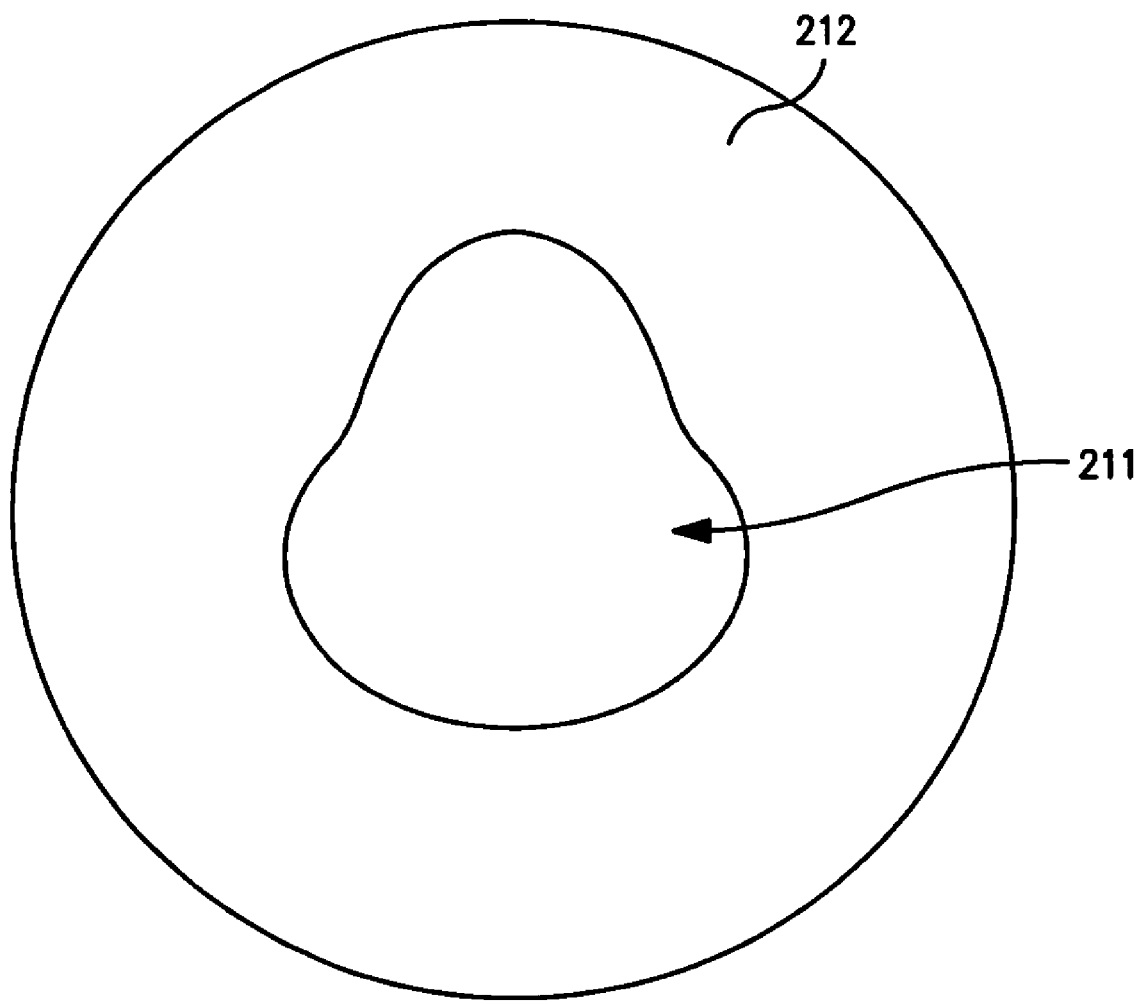
Figure 2R:
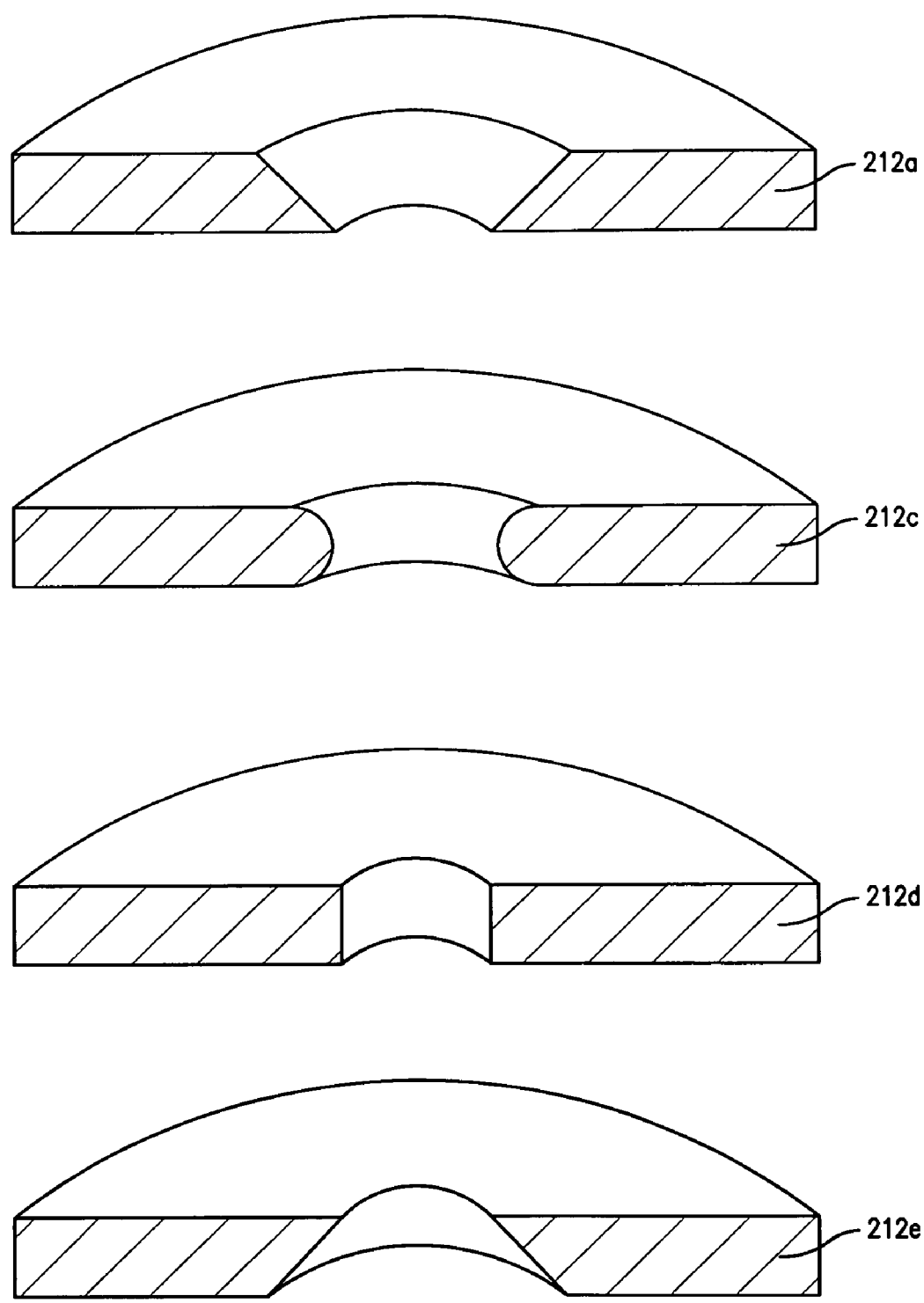
Figure 2S:
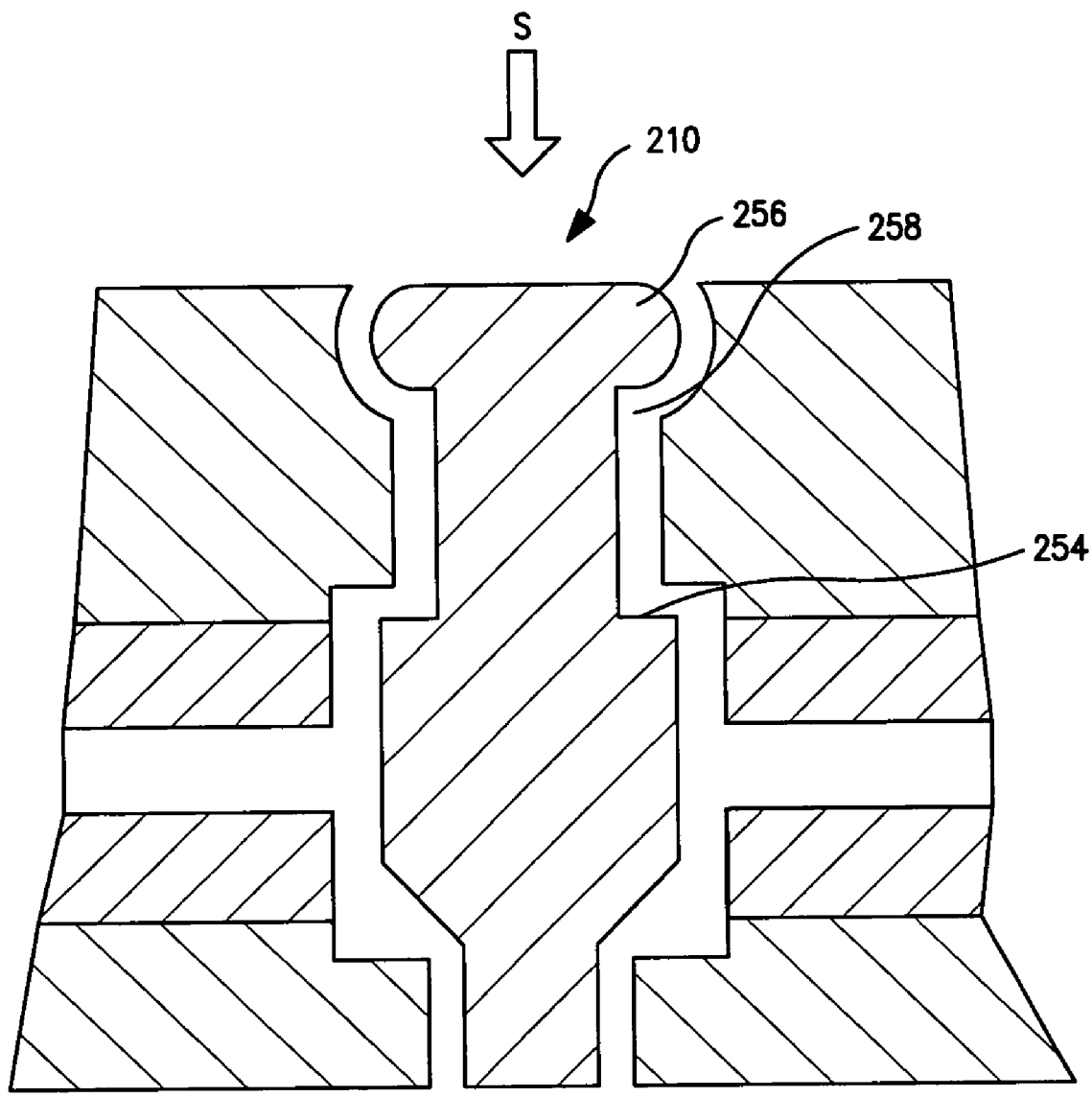

In one embodiment, the pivot 210 is permanently placed within the connector 200 via use of an interference fit arrangement, such as that illustrated in FIG. 2s. To effect the interference fit, the pivot 210 comprises a pin having an enlarged center portion 250 comprising an asymmetric configuration; e.g., a set of angled shoulders 252 and a set of squared shoulders 254 on opposing sides. Accordingly, when the pivot pin 210 is inserted in the direction given by arrow "S" of FIG. 2S, the angled shoulders 252 assist in guiding and advancing the pivot pin 210 through the pin channel 258 created by the nested body 202 and finger 204 components. The diameter of the channel 258 may also be adjusted relative to the diameter of the pin center portion 250, such that more or less friction is experienced upon insertion. The pivot pin 210 is fully inserted when it is level with the upper and lower surfaces of the connector 200 as shown, and comprises an enlarged cap portion 256 to prevent over insertion into the pin channel 258. When the pivot pin 210 is fully inserted, the squared shoulders 254 substantially frustrate movement of the pin 210 in the direction opposite that given by arrow "S", as these are shaped so as to substantially impede movement through the channel (versus the tapered or angled shoulders of the opposing side). Other alternative configurations may also be used in conjunction with the connector 200 of the present invention in order to provide such "one-way" insertion (i.e., ability to insert but not remove without substantially destroying the connector), the embodiment of FIG. 2s being merely exemplary.

FIG. 2p also illustrates an exemplary disposition of the metal contact plate 212. In the illustrated embodiment, the metal contact plate 212 is molded into the bottom platform 202b of the body in such a way so as to be disposed around the entirety of the sensor receiving aperture 211 (i.e., 360° around the opening of the aperture 211). It is noted that according to this embodiment, metal need not be disposed on the finger 204 of the connector 200. However alternative embodiments, including those having metal disposed in the V-shaped portion 208 (which comes into contact with the sensor 100) or elsewhere in the finger 204, are also readily appreciated by those of ordinary skill given the present disclosure.

Disposing metal around the opening of the aperture 211 advantageously increases the amount of surface area contact between the metal contact plate 212 and the sensor 100 as compared to other prior art connectors. Increased surface area of contact ensures adequate transmission of electrical current and/or voltage sensing, without undesirably high impedance due to the terminal/connector interface.

The metal used for the metal contact plate 212 may comprise any number of well known materials, such as e.g., Type 302 Stainless Steel (0.036 in. nominal diameter) having a nickel plating for added ruggedness and low friction. The passivated nature of the stainless steel (i.e., Chromium content) avoids corrosion or oxidation of the conductor element after formation; e.g., while it is sitting on the shelf waiting to be used. Such corrosion or oxidation might cause undesirable changes in the electrical properties of the conductor element, thereby reducing the accuracy and stability of the monitoring system as a whole. This is especially true considering the relatively small electrical potentials being measured in the typical ICG or ECG system. Furthermore, such corrosion and oxidation can increase the roughness or texture of the surface of the contact plate 212, thereby providing increased resistance to rotation of the connector 200 around the sensor terminal 100 during use, and may also conceivably affect pull-away force (discussed elsewhere herein).

The illustrated metal contact plate 212 is substantially circular in shape of its outer periphery as given in FIG. 2q. The interior periphery of the plate 212 comprises the eccentric or elongated shape previously described with respect to FIG. 2h. This interior shape is selected for a variety of reasons, including both the ability to translate the terminal shaft portion 104 laterally into the narrower portion of the aperture 211 thereby positively engaging it, as well as providing a smooth, low friction interface with the rounded sensor shaft 104, thus allowing for increased flexibility of use in that a clinician may rotate the connector about the sensor terminal 100. It will be appreciated, however, that other shapes may be used. For example, an octagonal, hexagonal, square or rectangular may be used with proper adaptation. Myriad other variations and combinations are possible, as will be recognized by those of ordinary skill in the art.

The cross-sectional profile of the aperture portion 211 of the metal contact plate 212 may also be adjusted. FIG. 2r illustrates several exemplary cross-sectional profiles which may be used in the present invention (note that these sections are taken across a region of the aperture 211 that does not include the aforementioned eccentric area). For example, the contact edge of the metal contact plate 212a may be beveled, chamfered or angled toward the sensor aperture 211; or away from the aperture 211 as shown in contact plate 212b. Alternatively, the contact plate may be rounded 212c or squared 212d with respect to its cross-sectional profile at the sensor aperture 211. Furthermore, the metal contact plate of the present invention may comprise various thicknesses (not shown), including tapering (i.e., becoming more or less thick closer or further from the aperture 211).

The ease with which the connector 200 is disconnected from a sensor terminal 100 without being actuated (i.e., without actuating the finger 204 toward the body 202) is affected by the shape and cross-sectional profile of the contact region (aperture 211) of the metal contact plate 212. Specifically, in the exemplary chamfered aperture 212a of FIG. 2r, the actual contact area between the plate 212 and the terminal shaft 100 is minimal in effect, only an edge. Therefore, torsional force on the connector (e.g., applied by lifting the connector cable up and away from the subject being monitored) will more readily cause the connector (and plate 212) to rotate with respect to the terminal, eventually causing the V-shaped stop 208 to retract as if the finger handle had been depressed to open the connector. The terminal 100 will eventually leverage the aperture open enough to release it from the connector aperture ("pull away"). In a similar manner, the shape of the contact region aperture 211, the contact plate 212 and/or of the V-shaped stop 208 may be adjusted to increase or decrease the pull-away force associated with a particular connector.

In one variant, the cross-sectional shape of the contact region of the aforementioned "V" notch or stop is altered (such as by more or less chamfer, changing the radius, polishing of the surfaces, etc.)

Pull away effects may also be adjusted by adjusting the tension of the spring associated with the spring-loaded pivot 210.

Moreover, the pull-away properties can be adjusted by variation of the Z-axis (vertical, as measured along the center axis of the sensor terminal) distance; i.e., where vertically the connector contacts the terminal on its shaft or shank.

It is appreciated that the aforementioned mechanisms for adjusting the ease with which the connector 200 is disconnected or pulled away from a sensor may advantageously be employed without subsequent modifications to the tooling of the connector. In other words, a manufacturer is not required to re-tool a connector 200 (e.g., modify molds or die) in order to adjust or change the pull-away characteristics of the production connector devices. Rather, modification of other attributes/components can be used to achieve the desired results.

"Large" Sensor Accepting Connector Apparatus—

Figure 3A:
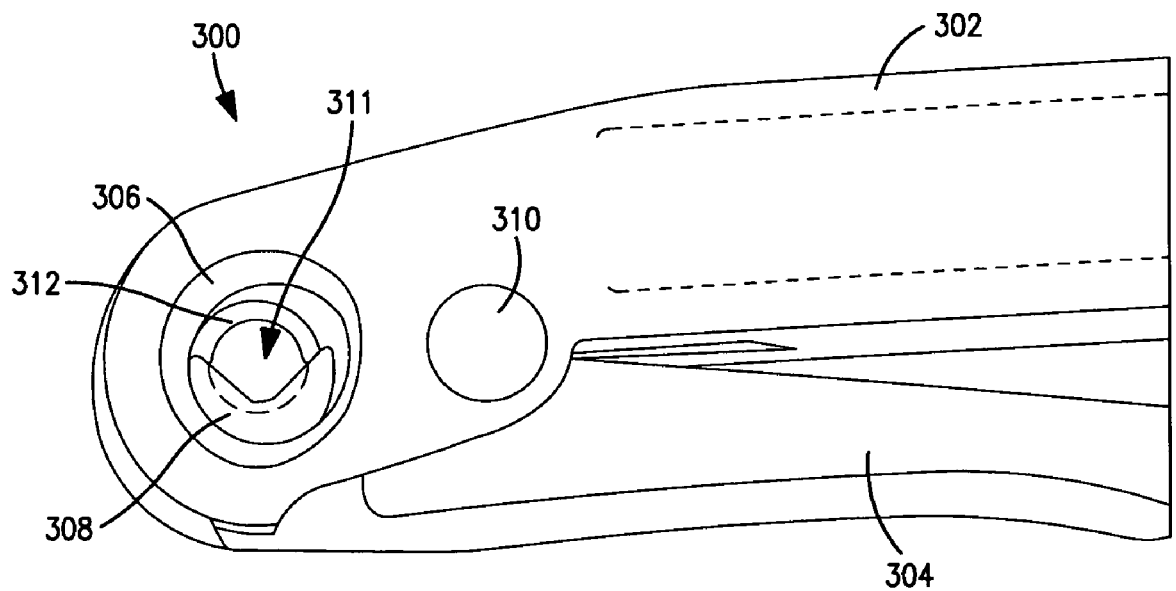
FIG. 3a is a top perspective view of an exemplary embodiment of the large sensor accepting connector apparatus of the present invention.
Figure 3B:
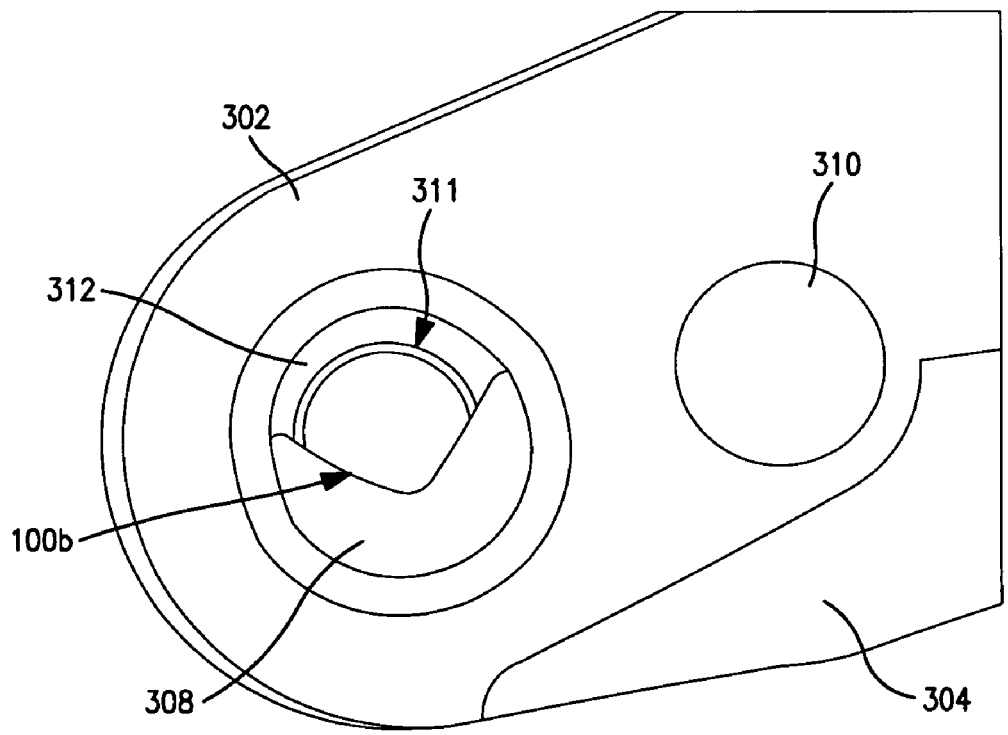
FIG. 3b-3c are top perspective views of the connector of FIG. 3a in the open position and having a small sensor accepted and illustrating the inability of the connector to hold or lock the small sensor.
Figure 3C:
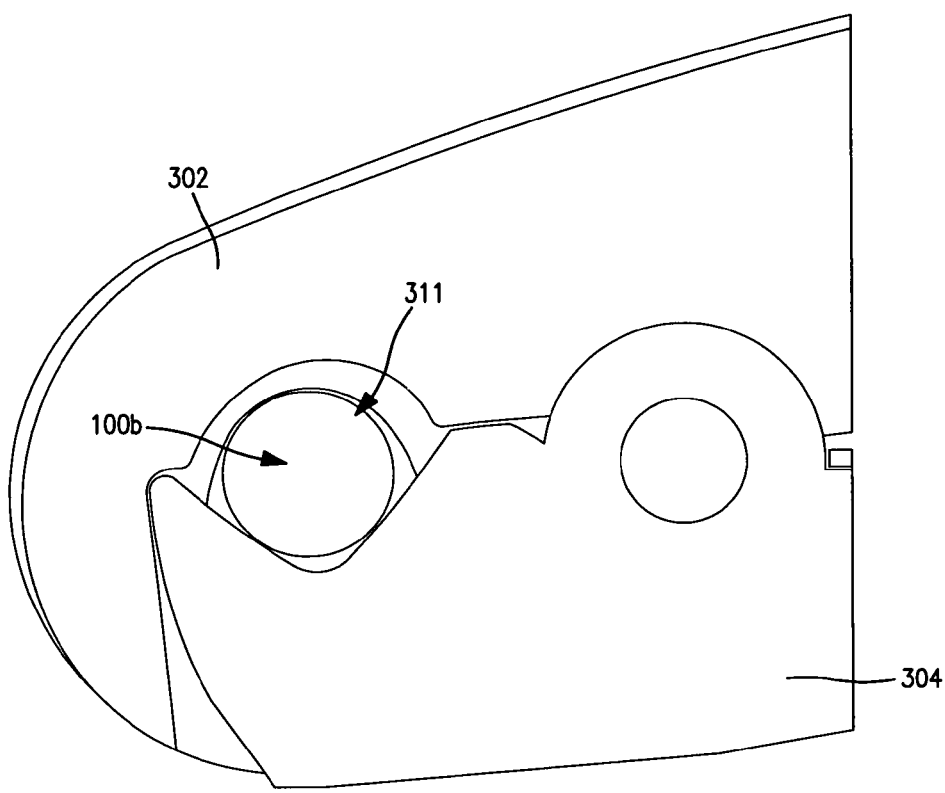
Figure 3D:
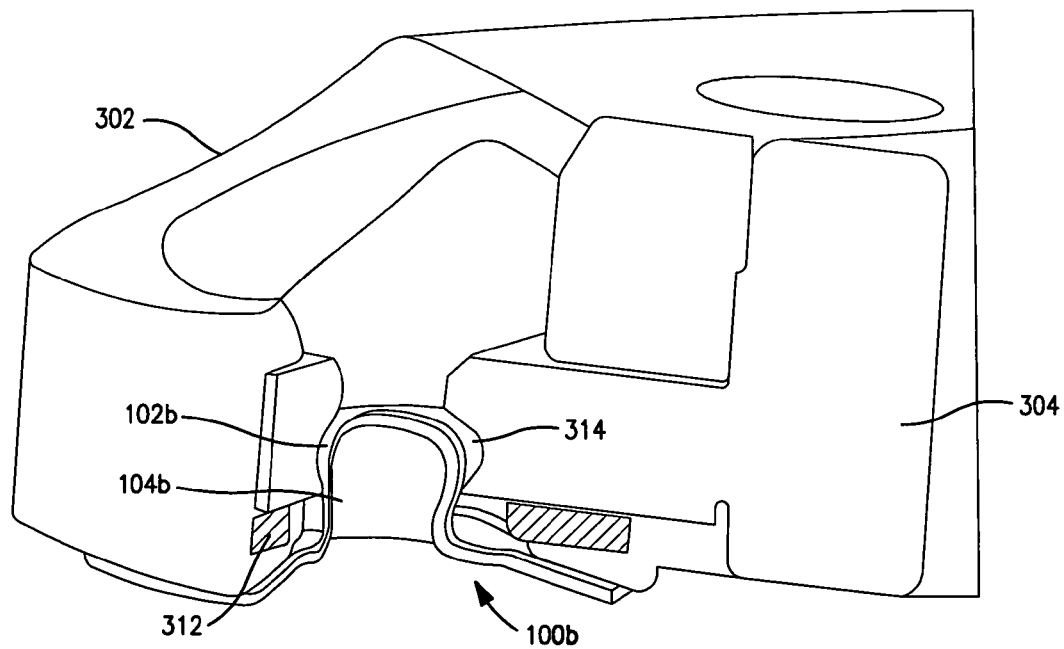
FIG. 3d-3e are cross-sectional views of the connector of FIG. 3a in the open position and having a small sensor accepted and illustrating the inability of the connector to hold or lock the small sensor.
Figure 3E:
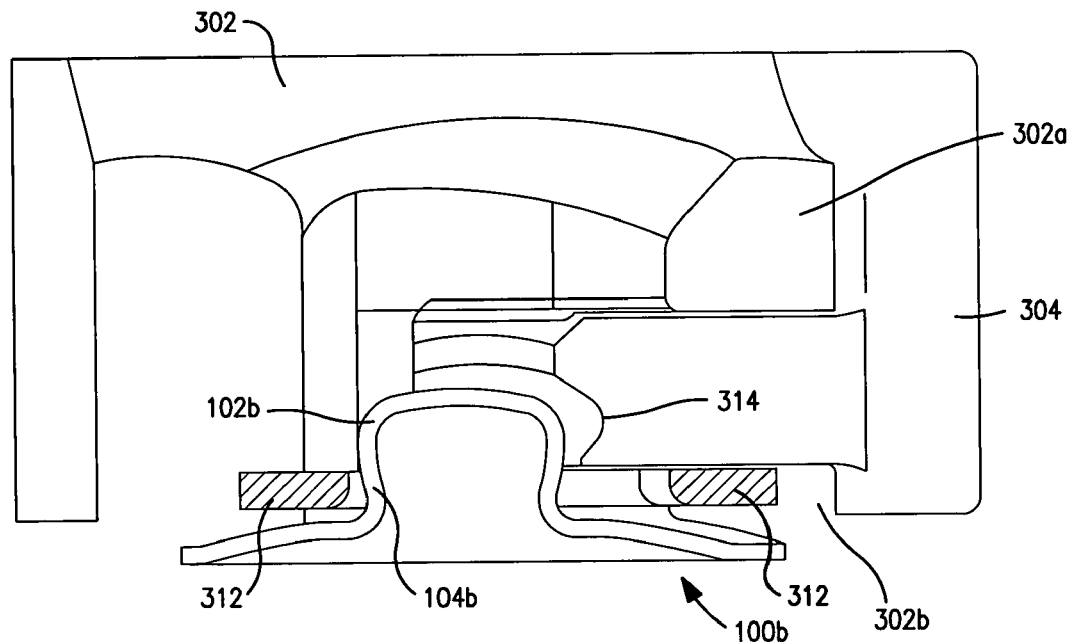
Figure 3F:
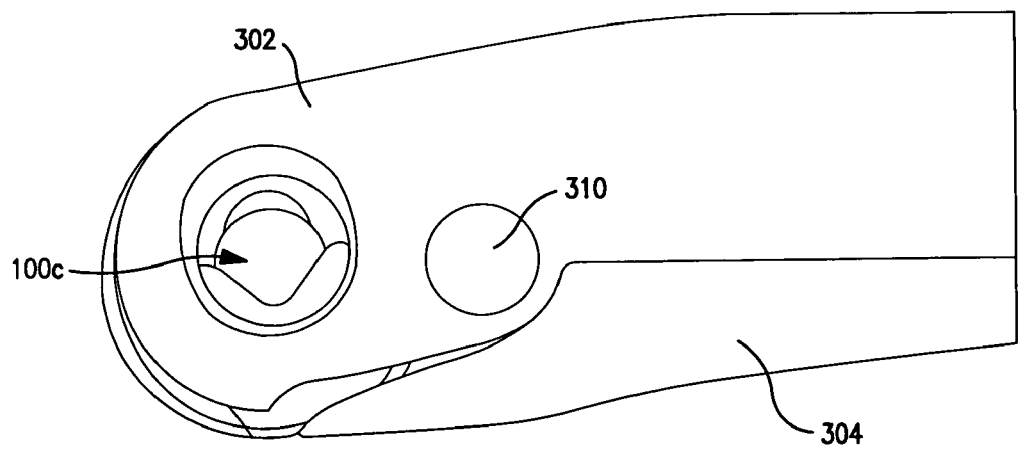
FIG. 3f is a top view of the connector of FIG. 3a in the open position and having a large sensor accepted.
Figure 3G:
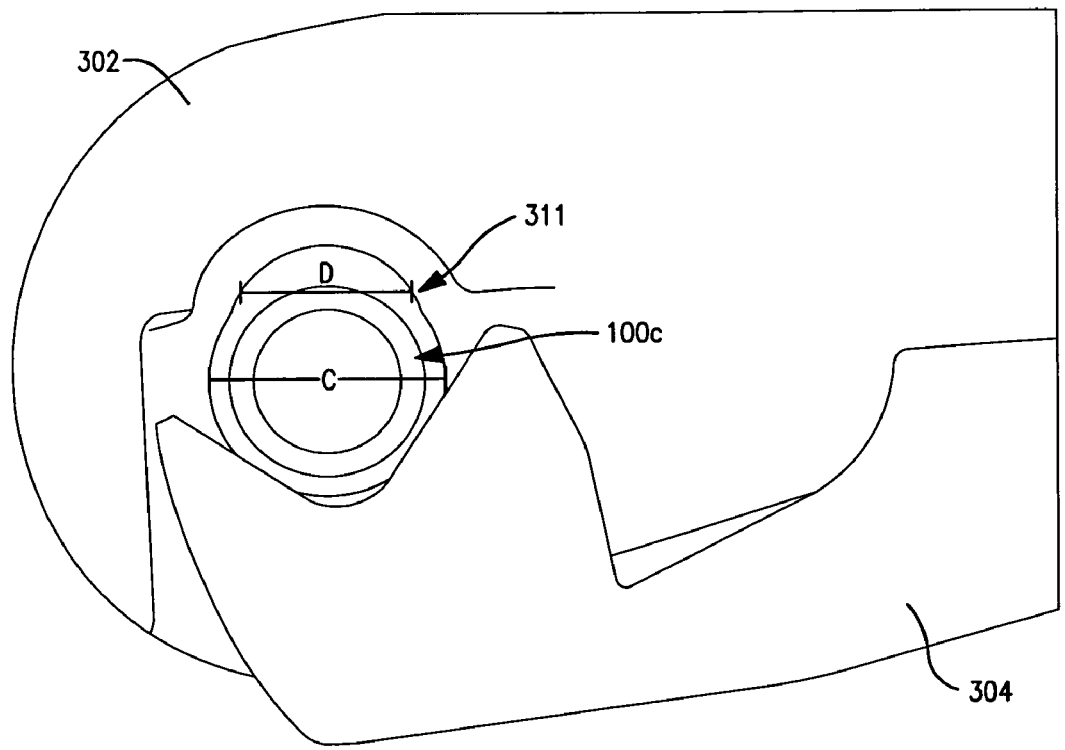
FIG. 3g is a top view of the connector of FIG. 3a in the open position and having the top platform layer removed and having a large sensor accepted.
Figure 3H:
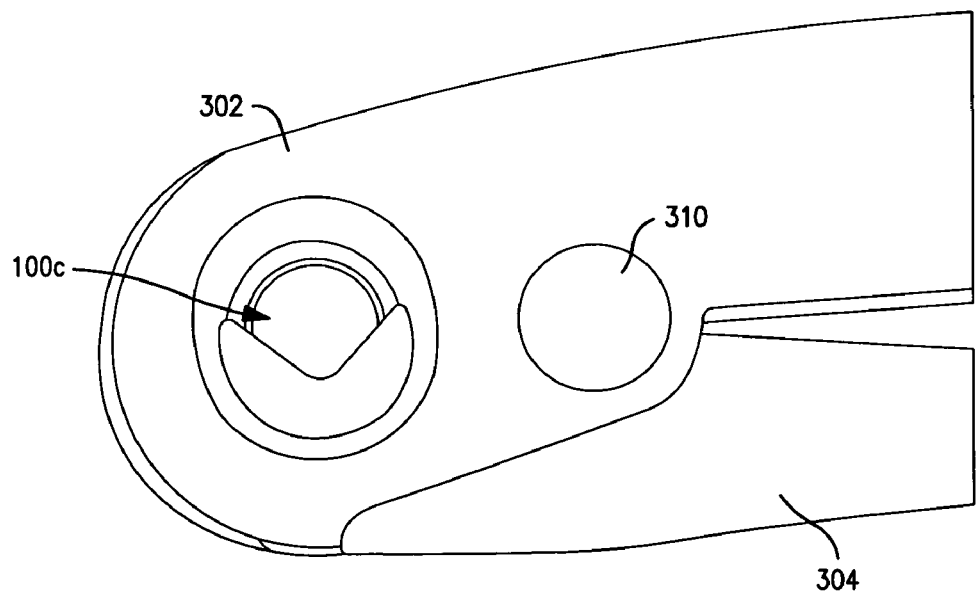
FIG. 3h is a top view of the connector of FIG. 3a in the closed position and having a large sensor accepted and held or locked in place.
Figure 3I:
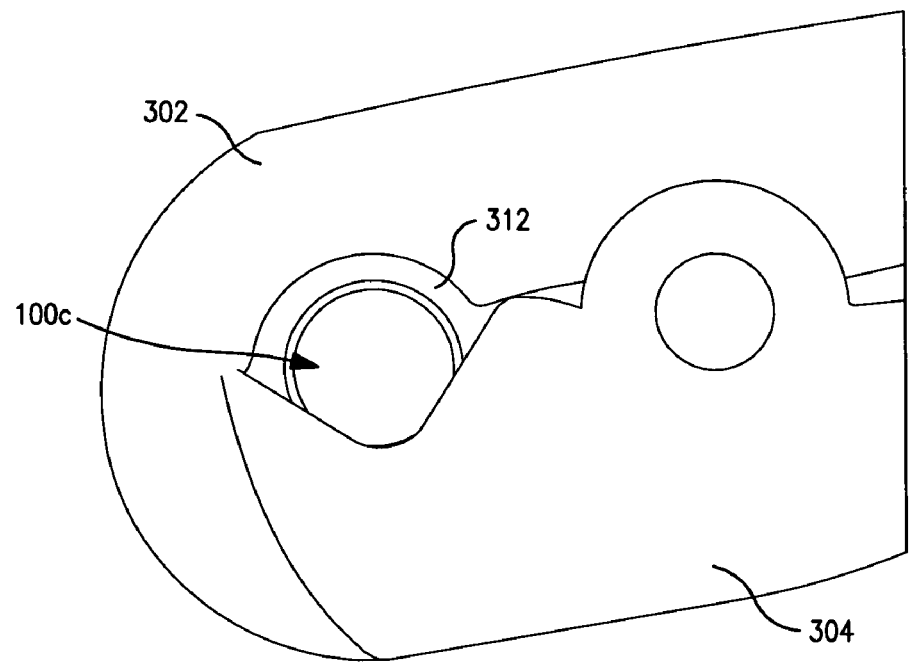
FIG. 3i is a top view of the connector of FIG. 3a in the closed position and having the top platform layer removed and having a large sensor accepted and held or locked in place.
Figure 3J:
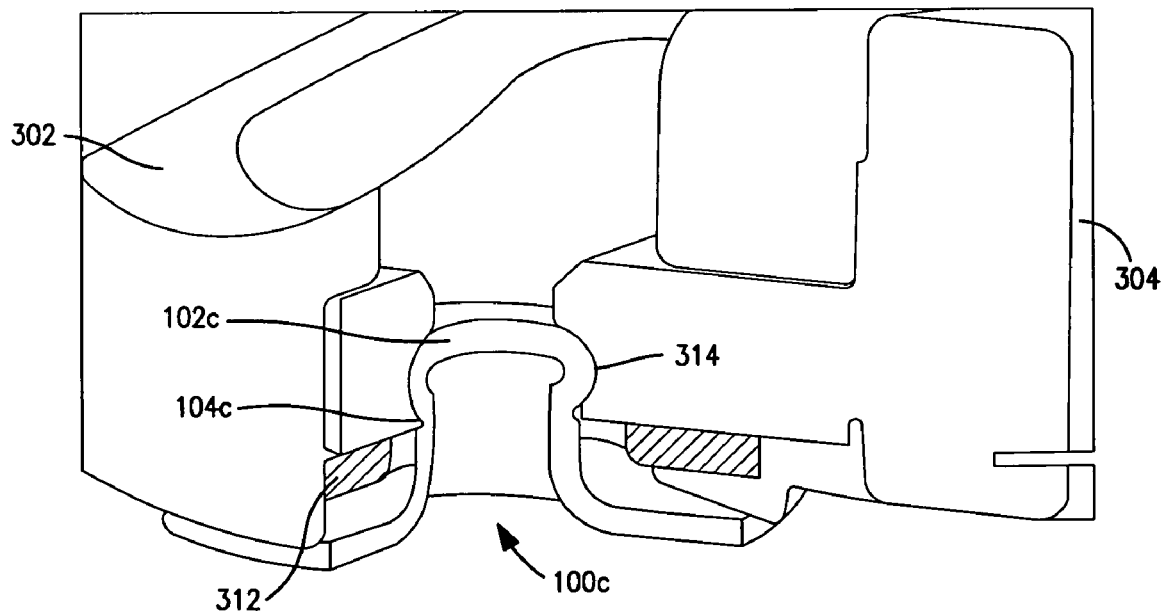
FIGS. 3j-3k are cross-sectional views of the connector of FIG. 3a in the closed position and having a large sensor accepted and held or locked in place.
Figure 3K:
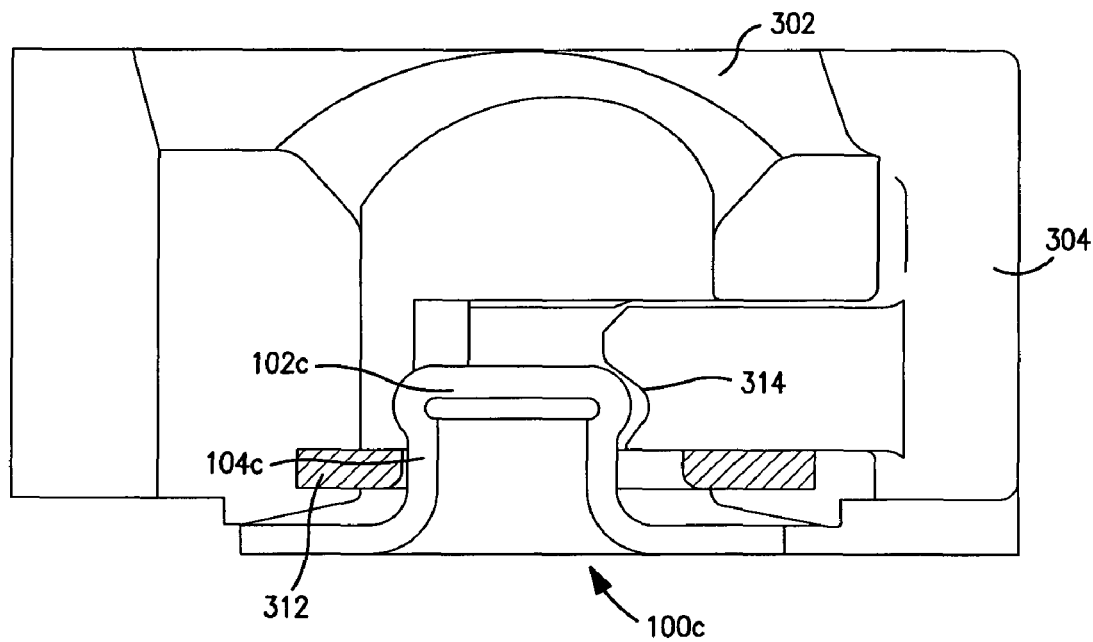
Figure 3L:
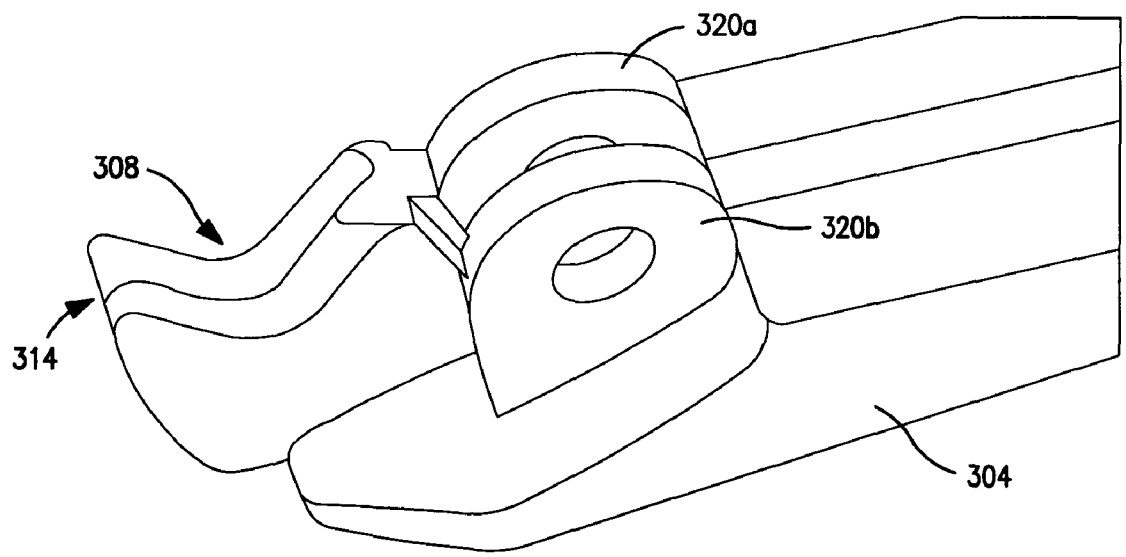
Figure 3M:
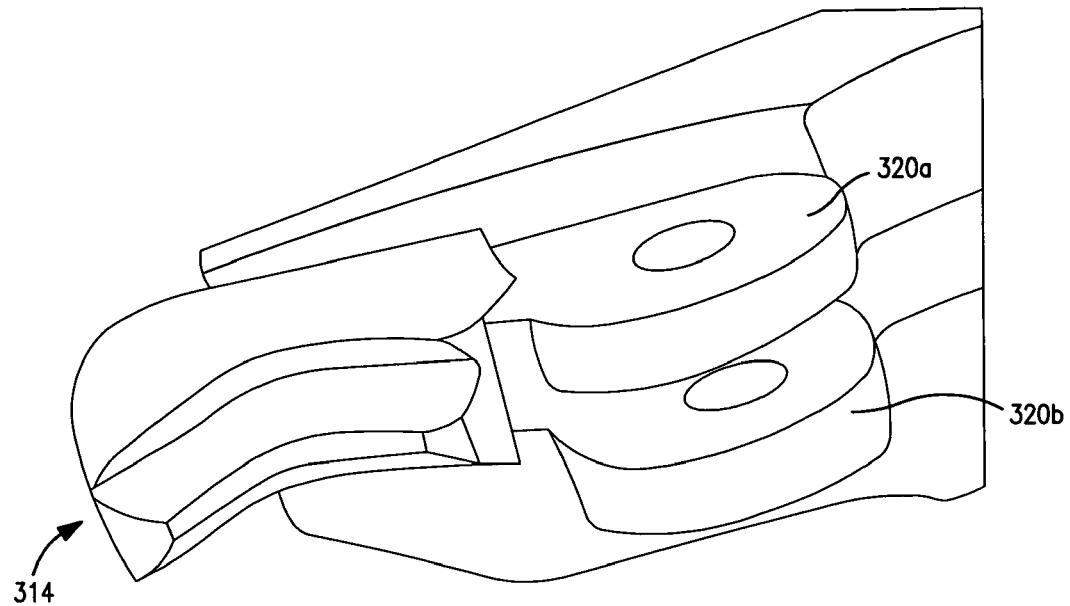
Figure 3N:
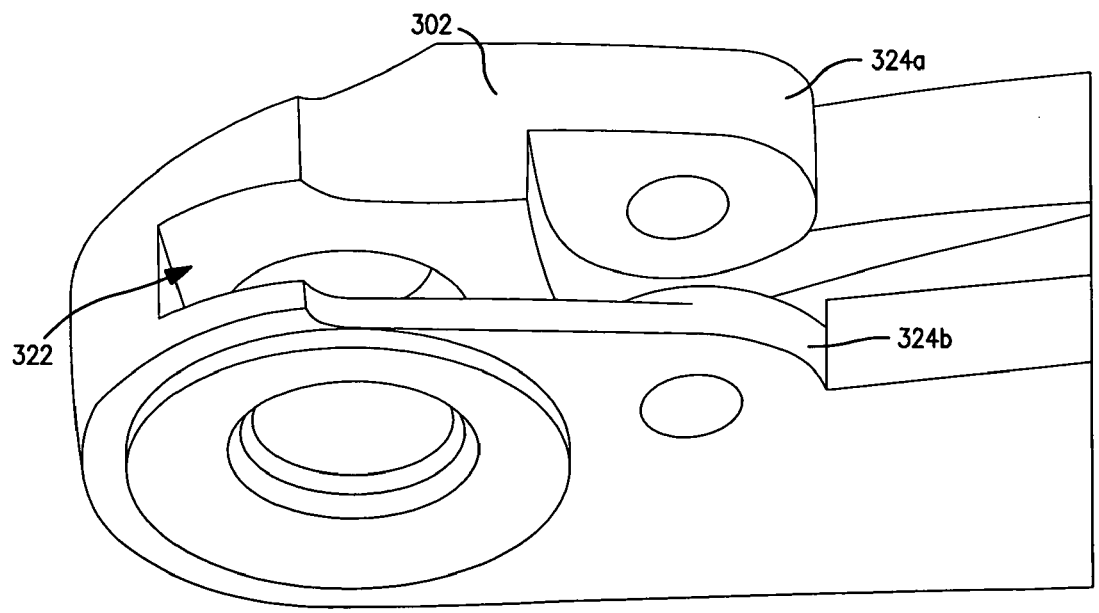
FIG. 3n-3o are side and bottom view perspective views, respectively, of the body portion of the connector of FIG. 3a illustrating the metal contact plate.
Figure 3O:
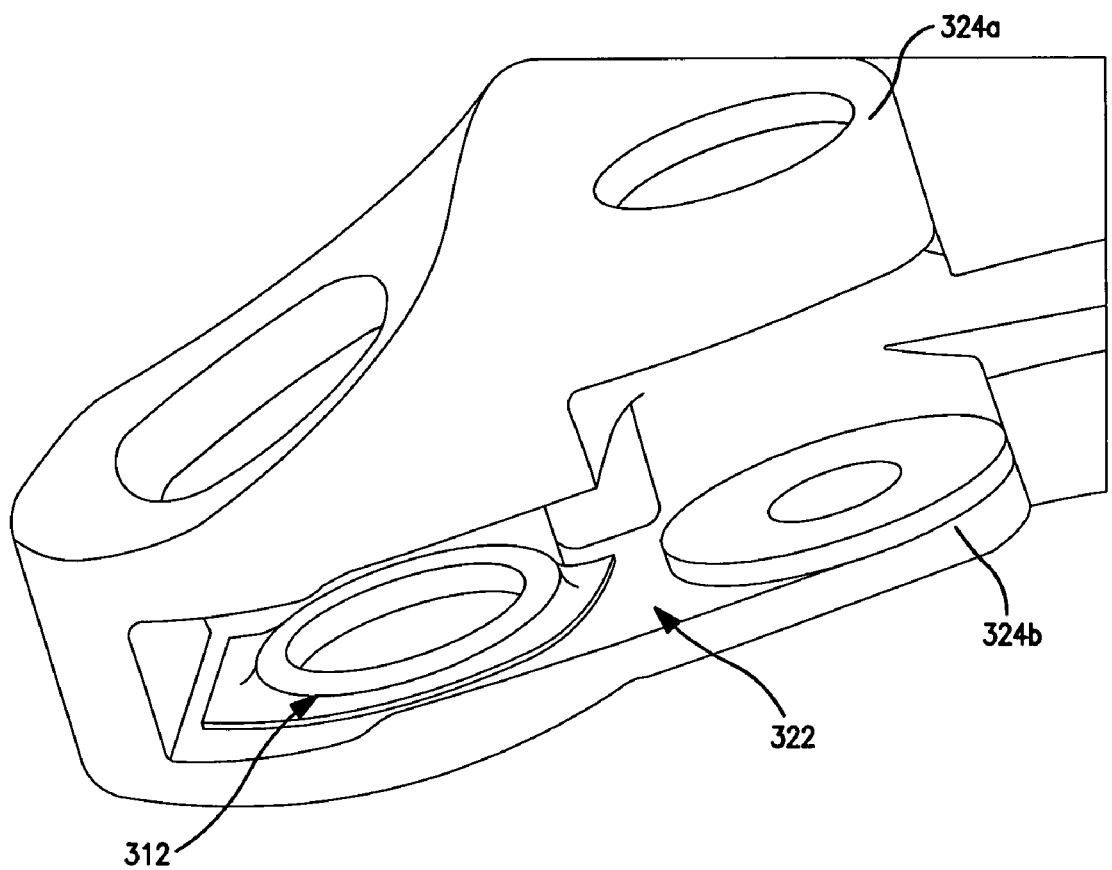

Referring now to FIGS. 3a-3o, another exemplary embodiment of a connector apparatus of the present invention is disclosed. The large sensor accepting connector apparatus 300 comprises many of the same features as the small sensor accepting connector 200 discussed above, as will be described in greater detail herein accordingly.

FIG. 3a illustrates an exemplary embodiment of the large sensor accepting connector apparatus 300 of the present invention. The exemplary connector apparatus 300 generally comprises two actuators: a connector body 302 and a finger 304; these components may comprise a molded polymer such as ABS (acrylonitrile butadine styrene), polyethylene, fluoropolymers (e.g., ETFE), or the like. The connector body 302 comprises a top and bottom platform 302a, and 302b within which the finger 304 is accepted. Further, as noted above with respect to FIG. 2b, the connector body 302 may further comprise one or more electrical resistors or other electrical components.

When mated, the body 302 and finger 304 rotate about a fixed pivot 310 and also form a sensor accepting aperture 311. It is appreciated that the pivot of the illustrated embodiment of the large sensor accepting connector 300, much like the small sensor accepting connector 200 described above, comprises no external stops. In one embodiment, the connector 300 comprises at least one internal stop which prevents the connector 300 from accepting a sensor terminal 100 of smaller size, as will be discussed below. The pivot is also permanently placed within the connector apparatus, thus substantially frustrating a user from changing the configuration of the internal stop (e.g., to accept sensor terminals of sizes other than those intended) without destroying the connector 300. In one variant, the pivot 210 comprises a pin such as that illustrated in FIG. 2s.

Also as noted above with respect to the smaller connector 200, the connector is biased to a closed position around the pivot, and requires force for opening the connector to increase the size of the aperture 311 in order to accept a sensor terminal. The shape of the aperture 311 is defined by a metal contact plate 312 associated with the body 302 and the V-shaped stop 308 of the finger 304. The body 302 also includes a chamfered or beveled dimple 306 which is chamfered inward toward the aperture 311 so as to provide optimum visibility from above at all azimuth angles when a user or clinician is placing the connector 300 on a sensor 100.

Referring now to FIGS. 3b-3e, the mechanism by which the exemplary large sensor accepting connector 300 is unable to lock into place a sensor 100 having a head with a diameter smaller than that which it is adapted to receive is described. In the illustrated embodiment, the connector 300 is adapted to receive a sensor terminal (not shown) having a head with a 0.185 in. diameter. However, in the illustrations of FIGS. 3b-3e, a smaller sensor 100b is shown—the smaller sensor terminal 100b has a 0.155 in. diameter head. It is appreciated that this diameter is merely exemplary and that the described concepts are equally applicable to any sensor terminal 100 having diameter smaller than the diameter which the connector 300 of the invention is adapted to receive.

The illustration of FIG. 3c gives a top view of a smaller sensor 100b disposed within the aperture 311 of an exemplary connector 300 which has the top platform 302 of the body 202 removed. As illustrated, when a user places the connector 300 in open position, i.e., when the V-shaped stop 308 of the finger is moved away from the center of the aperture 311 to permit entry of the cap 102 of a sensor terminal 100, the aperture opening is large enough to receive the cap 102b of the smaller sensor 10b. It is further appreciated that, depending on the size of the diameter of the cap 102, when the connector is returned to a closed position (as shown in FIG. 3c), an appreciable gap may still exist between the contact plate 312 and sensor 100b. In this fashion, the "large" connector will in effect not engage, and may even "fall off" the sensor terminal 100 that is sized too small.

Furthermore, as depicted in the cross-sectional views of FIGS. 3d-3e, the interior walls of the V-shaped portion 308 of the finger 304 are grooved 314 to conform to the cap 102 of an appropriately sized sensor 100. Thus, when the smaller (inappropriately sized) sensor 102b is received in the connector aperture 311 and the connector 300 placed in the closed position, the sensor cap 102b is not large enough to be engaged by the grooves 314, and thus be pushed by the finger 304 into the metal contact plate 312. Accordingly, no electrical contact is made between the smaller sensor 100b and metal contact plate 312, and the sensor 100b is loosely held within the connector (i.e., is not locked into place).

FIGS. 3f-3g illustrate the exemplary connector 300 in an open position and having a large sensor 100c accepted in the sensor aperture 311. As noted above with respect to FIG. 2h, the connector 300 of the present embodiment also comprises an aperture having two sections one having a larger diameter C, adapted to receive the cap 102 of an appropriately sized sensor 100, and the second section having a smaller diameter D, which is able to accommodate the shaft 104 of an appropriately sized sensor 100. In the present embodiment, the connector 300 is particularly adapted to receive a sensor sized 0.185 in., thus the first diameter C must be greater than (but within an acceptable range of) 0.185 in., while the second diameter D, is significantly smaller. When the connector 300 is closed, the finger 304 is adapted to engage the sensor cap 102c and push and hold the sensor 100c toward the metal contact plate 312.

Also depicted is the mechanism for allowing the cap 102c of a sensor 100c to enter the sensor aperture 311. As shown, the finger 304 comprises a V-shaped stop 308 which moves away from the center of the aperture 311 when the connector 300 is in the open position, thereby allowing the cap 102c of the sensor 100c to pass through the aperture 311.

FIGS. 3h-3k illustrate the exemplary large sensor accepting connector 300 in the closed position and having a large sensor 100c locked into place. The sensor 100c of the present embodiment is illustrated as having a 0.185 in. diameter head 102c; however alternate connector embodiments may be adapted to receive sensors 100c having smaller or larger head diameters as needed. As noted above, the connector 300 of the present embodiment also comprises a aperture having two sections one having a larger diameter adapted to receive the cap 102 of an appropriately sized sensor 100 and the second section having a diameter smaller than the first, yet able to accommodate the shaft 104 of an appropriately sized sensor 100. Thus, when the connector 300 is closed (as shown in FIGS. 3h-3k), the large sensor 100c is unable to disengage, as it is held in place by the grooved 314 finger 304, pushing the sensor 100c against the appropriately sized portion of the aperture of the metal contact plate 312. When the connector 300 is closed, the metal contact plate 312 and the V-shaped stop 308 maintain a aperture 311 which is only large enough for the sensor shaft 104c (not the sensor cap 102c). As illustrated, the cap 102a is disposed above the metal contact plate 312 and portions of it are received within the grooved portion 314 of the finger 304.

FIGS. 3l-3m illustrate the finger 304 in greater detail. As noted above and depicted, the V-shaped stop 308 has a grooved feature 314 for accommodating the cap 102c of a large sensor 100c. The finger 304 also comprises first and second pivot rings 320 which are adapted to encircle the pivot 310 and enable the finger 304 to rotate toward and away from the body 302 when mated therewith.

FIGS. 3n-3o illustrate the connector body 302 which forms (via the upper 302a and lower 302b platforms) a "cradle" 322 within which the finger 304 is disposed. The upper 302a and lower 302b platforms also comprise upper and lower pivot receiving apertures 324a and 324b, respectively, which receive the pivot 310 assembly (not shown) when the finger is mated therein.

The pivot 310 generally comprises a mechanism similar to that described above with respect to FIG. 2 (e.g., a spring-loaded pivot which causes the connector 300 to rest in a closed position).

The metal contact plate 312 is also illustrated in greater detail in FIG. 3o. As noted above with respect to FIG. 2p, the metal contact plate 312 may take one of many embodiments (such as those useful in increasing the surface area contact between the sensor 100c and connector 300). Further, the contact plate 312 may comprise any number of cross-sectional shapes and/or thicknesses such as those illustrated in FIG. 2r.

Method of Manufacture—

Referring now to FIG. 4, an exemplary embodiment of the method 400 of manufacturing the connector 200, 300 of the present invention is described in detail. It will be appreciated that while the following method is described primarily in terms of the connector embodiments of FIGS. 2a-2p and 3a-3o, the method can be readily adapted to any of the other embodiments shown or described herein (or contemplated by the broader principles of the invention) by those of ordinary skill in the manufacturing arts.

As shown in FIG. 4, the method 400 comprises first providing a metal contact plate 212, 312 (step 402). As previously described herein, the metal contact plate 212, 312 comprises a metallic (e.g., alloy) conductor having a selected cross-section (e.g., round, elliptical, rectangular, etc.). In step 404, body 202, 302 component is formed, such as via a molding process (e.g., injection, transfer, or the like). At step 406, the metal contact plate 212, 312 is disposed within the body 202, 302.

Per step 408, the finger 204, 304 component is formed and in one embodiment, a metal contact similar to that described above is optionally placed therein.

Then, at step 410, the body 202, 302 and finger 204, 304 components are nested together. At step 412, the spring-loaded pivot 210, 310 (including the spring) is placed within appropriate receiving apertures of the nested components, and is fixed in place via an interference fit. As discussed above, the interference fit arrangement may utilize a particularly shaped pivot pin 210 which is adapted to be inserted into the nested components in only one direction and which comprises features frustrating movement in the opposite direction (i.e., removal) once the pin has been inserted fully. The pivot pin 210 may further comprise an enlarged cap portion 256 to prevent insertion within the nested components past a particular point. However, alternative mechanisms for securing the pivot 210, 310 within the nested components may be used as well consistent with the present invention.

The assembled connector 200, 300 may then be mechanically and electrically tested (step 414); e.g., by mating the connector to a terminal or other electrically conductive device and performing electrical continuity or resistance testing thereof. For example, since the electrical characteristics of the connector are potentially critical in certain applications, the connector may be mated to an actual electrode of the type with which it will be used (e.g., ICG or ECG "patch" or spot electrode) and tested in this fashion, thereby most closely approximating actual operating conditions. The connector 200, 300 may also be tested for voltage withstand or other electrical, mechanical or insulating properties such as the aforementioned "pull away" force requirements. Myriad other testing and/or quality assurance techniques may be applied as desired.

Method of Use—

Referring now to FIG. 5, an exemplary method 500 of using a connector 200, 300 according to the present invention is disclosed. The method 500 comprises, at step 502 placing at least one sensor 100 on the skin of a patient. This may be for example a single or "ganged" ICG electrode assembly of the type previously described or referenced herein. At step 504, the connector 200, 300 is opened and the sensor terminal 100 is received within the aperture 211, 311 thereof. At step 506, the connector 200, 300 is subsequently closed and the sensor 100 locked into position. Lastly, per step 508, electrical current is provided to and/or voltage readings are obtained from the appropriate sensor 100.

It will be recognized that while certain aspects of the invention have been described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the invention disclosed and claimed herein.

While the above detailed description has shown, described, and pointed out novel features of the invention as applied to various embodiments, it will be understood that various omissions, substitutions, and changes in the form and details of the device or process illustrated may be made by those skilled in the art without departing from the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. An electrical connector adapted for use with a biomedical sensor of a particular size, said connector comprising:
    a first actuation element having at least one electrically conductive element associated therewith;
    a second actuation element, at least a portion of said second actuation element adapted to be mated with said first actuation element, said mating comprising forming at least one feature for receiving at least a portion of said sensor; and
    a pivot element adapted to enable said actuation elements to pivot with respect to one another, said pivoting causing an effective diameter of said feature for receiving said at least a portion of said sensor to adjust;
    wherein said pivot element is configured to ensure that, upon said pivoting of said actuation elements to a resting position without the presence of the sensor, said effective diameter of said feature is maintained at a pre-set amount corresponding to the particular size of the biomedical sensor.

2. The electrical connector of claim 1, wherein said pivot element is adapted to ensure that said effective diameter of said feature is said pre-set amount via one or more internal stopping features.

3. The electrical connector of claim 2, wherein said one or more internal stopping features are not accessible to a user of said connector when said actuation elements are mated.

4. The electrical connector of claim 1, wherein said pre-set amount comprises approximately 0.125 inches.

5. The electrical connector of claim 1, wherein said pre-set amount comprises approximately 0.155 inches.

6. The electrical connector of claim 1, wherein said mating of said actuation elements further comprises forming at least one channel adapted to receive said pivot element, and wherein said connection of said actuation elements by said pivot element comprises permanently receiving said pivot element within said channel.

7. The electrical connector of claim 6, wherein said receipt of said pivot element in said channel is made permanent by an asymmetric shaped portion of said pivot element such that once said pivot element is received within said channel, said asymmetric portion substantially prevents said pin element from being removed.

8. The electrical connector of claim 1, wherein said at least one electrically conductive element associated with said first actuation element comprises a metallic disk molded onto a surface thereof, said disk placed on said first actuation element so as to comprise at least a portion of said feature for receiving at least a portion of said sensor.

9. The electrical connector of claim 8, wherein said disk is at least partly chamfered along a contact surface thereof.

10. The electrical connector of claim 1, wherein said first actuation element further comprises at least one resistor disposed therein, said resistor adapted to dissipate energy.

11. The electrical connector of claim 10, wherein said at least one resistor does not dissipate more than ten percent (10%) of the total energy provided to said connector.

12. The electrical connector of claim 1, wherein said second actuation element further comprises at least one electrically conductive surface, said electrically conductive surface disposed proximate to said at least one feature for receiving said at least a portion of said sensor.

13. An electrical connector adapted to be employed in conjunction with a biomedical sensor comprising at least one terminal composed of a shaft portion and a crown portion disposed at one end of said shaft portion, said crown portion having a greater diameter than said shaft portions, said electrical connector comprising:
    at least first and second body elements adapted to be pivotally mated to one another, the first of said body elements having at least one electrically conductive portion, and said mating of said body elements causing formation of at least two apertures; and
    at least one spring-loaded pivot element adapted to be received within a first of said apertures and enabling said body elements to pivot with respect to one another, said pivoting of said body elements causing a second of said apertures to be widened and narrowed;
    wherein said second aperture is adapted to removably receive at least a portion of said sensor therein, said widening of said second aperture enabling said at least a portion of said sensor to be received or removed and said narrowing of said second aperture enabling a sensor received therein to be substantially secured in place due to the first body element engaging primarily the sensor shaft portion and the second body element engaging primarily the sensor crown portion; and
    wherein modification of one or more components of said connector apparatus causes adjustment of an amount of force required to dislodge said electrical connector from said sensor.

14. The electrical connector of claim 13, wherein said amount of force required to dislodge said electrical connector from said sensor is adjusted to cause said connector to conform with the pull-away requirements of an ANSI/AAMI EC 53-1995 Standard.

15. The electrical connector of claim 13, wherein said one or more components comprises at least said electrically conductive portion of said first body element, and wherein said modification comprises at least one of:
    chamfering at least a portion of said electrically conductive portion; or
    changing a shape of said electrically conductive portion.

16. The electrical connector of claim 13, wherein:
    the second of said body elements comprises, proximate to said second aperture, a second body element surface conforming to a surface of the crown of said received sensor.

17. The electrical connector of claim 16, further comprising:
    a mechanism for restraining said at least a portion of said sensor comprising a substantially V-shaped extension of said second body element, said substantially V-shaped extension adapted to receive said sensor proximate to a junction between said crown and said shaft portion of said sensor, and
    said substantially V-shaped extension is further adapted to push said sensor into contact with said electrically conductive portion of said first body element.

18. The electrical connector of claim 17, wherein said mechanism for restraining said sensor further comprises an electrically conductive portion.

19. The electrical connector of claim 16, wherein said modification comprises changing the second body element surface.

20. The electrical connector of claim 13, wherein said one or more components comprises said spring-loaded pivot element, and wherein said modification comprises changing a tension of said spring-loaded pivot element.

21. The electrical connector of claim 13, wherein said receipt of said at least one spring-loaded pivot element into said first aperture is effected by said spring-loaded pivot element comprising a shape having one or more angular features adapted to interact with said aperture to substantially frustrate removal of said pivot element after insertion into said aperture.

22. An electrical connector adapted for use with a biomedical sensor comprising at least one terminal composed of a shaft portion and a crown portion disposed at one end of said shaft portion, said crown portion having a greater diameter than said shaft portion, said electrical connector comprising:
two pivotally mated elements:
said first element comprising at least one electrically conductive region adapted to accept at least a portion of said sensor terminal; and
said second element comprising at least one terminal confining region, said terminal confining region adapted to substantially maintain a position of said terminal relative said first element via application of force primarily against said crown portion of said terminal;
at least one pivot element about which said elements are adapted to pivot; and
at least one pivot obstruction feature adapted to impede said pivoting of said elements in at least one direction, said pivot obstruction feature limiting movement of said elements such that they may pivot no more than a distance substantially equal to said diameter of said neck portion of said terminal.

23. The electrical connector of claim 22, wherein said diameter of said crown portion is approximately 0.125 inches.

24. The electrical connector of claim 22, wherein said diameter of said crown portion is approximately 0.155 inches.

25. The electrical connector of claim 22, wherein said force applied to said sensor by said second moveable element comprises a force generated by a spring associated with said pivot element.

26. The electrical connector of claim 22, wherein said pivot element is permanently disposed within an opening formed by the mating of said moveable elements, said pivot element comprising at least one asymmetric region, said asymmetric region allowing said pivot element to be inserted within said opening, but also frustrating removal of said pivot element from said opening.

27. The electrical connector of claim 22, wherein said second moveable element further comprises an electrically conductive surface disposed proximate to said terminal confining region.

28. The electrical connector of claim 22, wherein said first moveable element further comprises at least one resistor, said resistor adapted to dissipate defibrillation or other electrical energy in accordance with the requirements of an ANSI/AAMI EC 53-1995 Standard.

29. The electrical connector of claim 22, wherein said at least one electrically conductive region of said first moveable element comprises a metallic plate molded onto a surface thereof, said plate having a cross-sectional profile, at least a portion of which that is obliquely angled with respect to a plane of said metallic plate.

30. The electrical connector of claim 22, wherein said electrical connector is further adapted to be dislodged from said received sensor at a force which is adjustable via incorporation of one or more modifiable components.

31. The electrical connector of claim 30, wherein said modification comprises changing a shape or cross-sectional profile of at least one of said one or more modifiable components.

32. An electrical connector for use in biomedical applications having at least two terminals each with different diameters, the connector comprising:
first and second body elements pivotally mated to one another; and
a variable-geometry aperture, the geometry of said aperture being controlled at least in part by pivoting of said first and second body elements;
wherein said variable-geometry aperture is configured to:
(i) allow a first of said terminals having a first diameter to be received within said aperture and confined within the aperture by a terminal confining region of the second body element adapted to substantially maintain a position of said first terminal relative said first body element via application of force primarily against a crown portion of said first terminal; and
(ii) prevent a second of said terminals having a second diameter to be received within said aperture; and
wherein said first diameter is smaller than said second diameter.

33. The connector of claim 32, wherein said first terminal comprises an ICG (impedance cardiography) terminal, and said second terminal comprises an ECG (electrocardiography) terminal.

34. The connector of claim 33, wherein said first diameter comprises 0.125 in., and said second diameter comprises 0.155 in.

35. The connector of claim 33, wherein said prevention of said second of said terminals having a second diameter to be received within said aperture is provided at least in part by a stop apparatus, said stop apparatus limiting travel of said first and second body elements relative to one another.

36. An electrical connector for use in biomedical applications having at least two terminals each with different diameters, the connector comprising:
first and second body elements pivotally mated to one another; and
a variable-geometry aperture, the geometry of said aperture being controlled at least in part by pivoting of said first and second body elements;
wherein said variable-geometry aperture is configured to:
(i) allow a first of said terminals having a first diameter to be received within said aperture and confined within the aperture by a terminal confining region of the second body element adapted to substantially maintain a position of said first terminal relative said first body element via application of force primarily against a crown portion of said first terminal; and
(ii) prevent a second of said terminals having a second diameter to be securely grasped within said aperture; and
wherein said first diameter is larger than said second diameter.

37. The connector of claim 36, wherein said first terminal comprises an impedance cardiography (ICG) terminal, and said second terminal comprises an electrocardiography (ECG) terminal.

38. The connector of claim 37, wherein said first diameter comprises 0.185 in., and said second diameter comprises 0.155 in.

39. The connector of claim 37, wherein said prevention of said second of said terminals having a second diameter to be securely grasped within said aperture is provided at least in part by a stop apparatus, said stop apparatus limiting travel of said first and second body elements relative to one another.

40. The electrical connector of claim 1, wherein the biomedical sensor comprises at least one terminal composed of a shaft portion and a crown portion disposed at one end of said shaft portion, said crown portion having a greater diameter than said shaft portion; and wherein at least one of the actuation elements having a surface adapted to primarily engage the sensor crown portion when a sensor is disposed within the at least one feature for receiving at least a portion of said sensor.

* * * * *